US011035825B2

(12) United States Patent
Carbonelli et al.

(10) Patent No.: US 11,035,825 B2
(45) Date of Patent: Jun. 15, 2021

(54) SENSING SYSTEMS AND METHODS FOR THE ESTIMATION OF ANALYTE CONCENTRATION

(71) Applicant: Infineon Technologies AG, Neubiberg (DE)

(72) Inventors: Cecilia Carbonelli, Munich (DE); Prashanth Makaram, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 624 days.

(21) Appl. No.: 15/813,687

(22) Filed: Nov. 15, 2017

(65) Prior Publication Data
US 2019/0145929 A1 May 16, 2019

(51) Int. Cl.
G01N 27/49 (2006.01)
G01N 33/00 (2006.01)
G01N 27/407 (2006.01)
G01N 27/12 (2006.01)

(52) U.S. Cl.
CPC ............ *G01N 27/49* (2013.01); *G01N 27/12* (2013.01); *G01N 27/125* (2013.01); *G01N 27/4071* (2013.01); *G01N 33/0006* (2013.01); *G01N 33/0031* (2013.01); *G01N 33/0034* (2013.01); *G01N 33/0042* (2013.01); *G01N 33/0062* (2013.01)

(58) Field of Classification Search
CPC ...... G01N 27/49; G01N 27/12; G01N 27/125; G01N 27/4071; G01N 33/0006; G01N 33/0031; G01N 33/0034; G01N 33/0042; G01N 33/0062
See application file for complete search history.

(56) References Cited

U.S. PATENT DOCUMENTS

| 5,609,096 A | 3/1997 | Kwon et al. |
| 2010/0286929 A1 | 11/2010 | Homer et al. |

FOREIGN PATENT DOCUMENTS

| DE | 19732501 C1 | 12/1998 | |
| JP | 3169715 B2 * | 5/2001 | |
| JP | 2003065988 A | 3/2003 | |
| WO | WO-0037933 A1 * | 6/2000 | ......... G01N 33/0031 |

OTHER PUBLICATIONS

Lipatov, Alexey et al., "Highly Selective Gas Sensor Arrays Based on Thermally Reduced Graphene Oxide," Nanoscale, Feb. 11, 2013, 11 pages.

(Continued)

*Primary Examiner* — Maris R Kessel
(74) *Attorney, Agent, or Firm* — Slater Matsil, LLP

(57) ABSTRACT

A method of gas sensing includes obtaining a first signal by a gas sensor, generating one or more second signals according to the first signal, and calculating a first weight value corresponding to the first signal. The first signal indicates a response of the gas sensor to a concentration of a target gas at the gas sensor. The method of gas sensing further includes calculating one or more second weight values corresponding to each of the one or more second signals and calculating an estimated concentration of the target gas at the gas sensor according to the first weight value and the one or more second weight values.

22 Claims, 15 Drawing Sheets

(56) References Cited

OTHER PUBLICATIONS

Vergara, Alexander et al., "Optimized Feature Extraction for Temperature-Modulated Gas Sensors," Journal of Sensors, vol. 2009, Article ID 716316, Jan. 26, 2009, 11 pages.
Roussel, Sylvie et al., "Optimisation of electronic nose measurements, Part I: Methodology of output feature selection," Journal of Food Engineering, vol. 37, No. 2, Nov. 9, 1998, pp. 207-222.
Llobet, Eduard et al., "Qualitative and quantitative analysis of volatile organic compounds using transient and steady-state responses of a thick-film tin oxide gas sensor array," Sensors and Actuators B 41, Jun. 1, 1997, pp. 13-21.
Wang, Tao et al., "A Review on Graphene-Based Gas/Vapor Sensors with Unique Properties and Potential Applications," Nano-Micro Letters, vol. 8 No. 2, Nov. 2015, pp. 95-119.

\* cited by examiner

SENSING SYSTEMS AND METHODS FOR THE ESTIMATION OF ANALYTE CONCENTRATION

TECHNICAL FIELD

The present invention relates generally to a sensing system, and, in particular embodiments, to a sensing system and methods for the estimation of an analyte concentration in the sensing system.

BACKGROUND

Sensing systems including sensor devices such as resistive gas sensors can detect the presence of target analytes in an ambient environment. It may be important to design sensing systems with the ability to output detection events in real-time with high sensitivity. Sensing systems may also be designed for high accuracy and specificity with respect to a target analyte or group of target analytes. In the specific case of resistive gas sensors, detection events may be based on the change in resistance or capacitance of a semiconducting thin-film structure that is influenced by the adsorption of gas molecules.

As the sensitivity of a sensing system improves, the influence of external environmental factors on the sensing system may also increase. Such environmental factors may include temperature, humidity, composition and concentration of species in the ambient atmosphere, and electromagnetic interference, among others. High sensitivity to external environmental factors may decrease sensing accuracy. Therefore, sensing systems which can reliably cope with calibration inaccuracies, sensor drift, and other similar effects over a wide operating range may be desirable in order to provide both high sensitivity and high accuracy.

SUMMARY

In accordance with an embodiment of the invention, a method of gas sensing includes obtaining a first signal by a gas sensor, generating one or more second signals according to the first signal, and calculating a first weight value corresponding to the first signal. The first signal indicates a response of the gas sensor to a concentration of a target gas at the gas sensor. The method of gas sensing further includes calculating one or more second weight values corresponding to each of the one or more second signals and calculating an estimated concentration of the target gas at the gas sensor according to the first weight value and the one or more second weight values.

In accordance with another embodiment of the invention, a method of gas sensing includes obtaining a first signal by a gas sensor and generating one or more second signals according to the first signal. The first signal indicates a response of the gas sensor to a concentration of a target gas at the gas sensor. The method further includes determining a first condition in which a concentration of the target gas is increasing at the gas sensor using the first signal and the one or more second signals. The method also includes determining a second condition in which the concentration at the gas sensor is substantially constant using the first signal and the one or more second signals. The second condition occurs after the first condition. The method further includes calculating a concentration value of the target gas according to the first signal and the one or more second signals, the calculating performed while the concentration is substantially constant.

In accordance with still another embodiment of the invention, a gas sensing system includes a gas sensor, a processor operatively coupled to the gas sensor, and a memory storing a program to be executed by the processor. The gas sensor is disposed on a first substrate and is configured to detect a target gas. The gas sensor is further configured to generate a first signal indicating a response of the gas sensor to a concentration of a target gas at the gas sensor. The program includes instructions for generating one or more second signals according to the first signal, calculating a first weight value corresponding to the first signal, calculating one or more second weight values corresponding to each of the one or more second signals, and calculating a concentration of the target gas at the gas sensor according to the first weight value and the one or more second weight values.

BRIEF DESCRIPTION OF THE DRAWINGS

For a more complete understanding of the present invention, and the advantages thereof, reference is now made to the following descriptions taken in conjunction with the accompanying drawings, in which.

Figure 1:
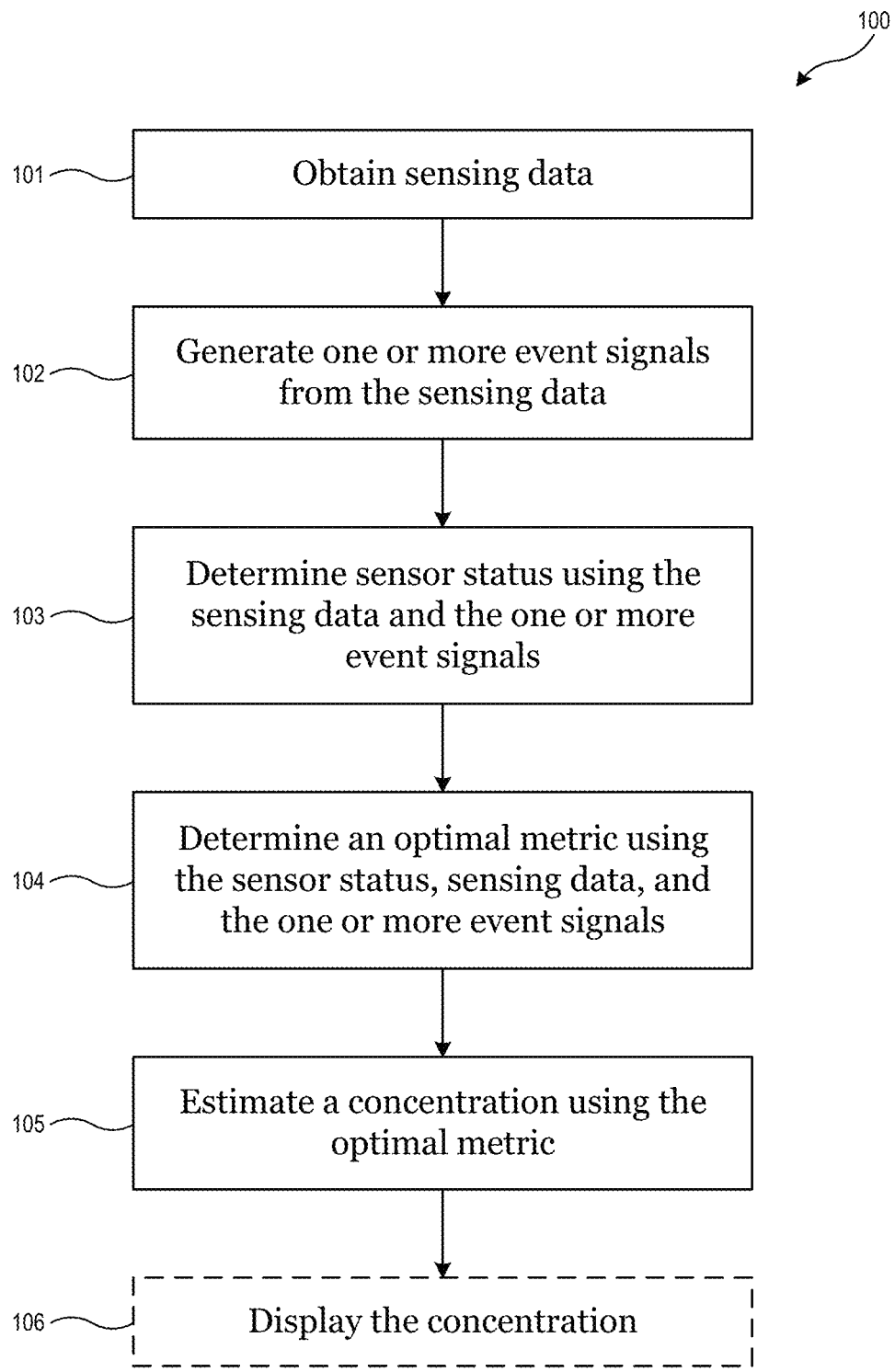
FIG. 1 illustrates an example method of estimating a concentration of a target analyte by a sensing system in accordance with an embodiment of the invention.

Corresponding numerals and symbols in the different figures generally refer to corresponding parts unless otherwise indicated. The figures are drawn to clearly illustrate the relevant aspects of the embodiments and are not necessarily drawn to scale. The edges of features drawn in the figures do not necessarily indicate the termination of the extent of the feature.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Sensing systems may be designed to detect concentrations of a target analyte at one or more sensors by determining the deviation of a measured value from a baseline value. For example, in gas sensing system, electrical resistance of a sensor may be used as a measured value to estimate concentrations of target gases. For example, the baseline or reference resistance may be on the order of 1 kΩ, for example, when no target gases are present. Concentrations of target gases at the sensor may then be estimated by comparing the sensor resistance to the value of 1 kΩ.

However, external factors that are not necessarily related to the concentration of target analytes at the sensor such as environmental factors may affect the sensing system. These external factors may negatively impact the accuracy of target analyte concentrations estimated using only a single measured value. For example, sensors such as chemoresistive gas sensors may have intrinsic instability that depends on the ambient environment. Therefore, a sensing system that uses additional information to increase accuracy when estimating concentrations of target analytes may be advantageous.

According to various embodiments, a sensing system is implemented that obtains a first signal in response to a concentration of a target analyte at a sensor. Next, one or more event signals are generated from the first signal that include information about the temporal evolution of the system. Thus, the first signal and the event signals represent possible metrics that may be used by the sensing system to calculate an estimation of the concentration of a target analyte present at the sensor. The sensing system may also compare the first signal and the event signals to threshold values to determine an optimal metric for calculating the concentration. Alternatively, the sensing system may assign weight values to each of the event signals and the first signal that are determined according to comparisons of the first signal and the event signals to the threshold values. Therefore, the weight values represent adjustments to the individual contributions of each of the metrics associated with the first signal and the event signals. An estimation of the concentration of the target analyte is then calculated by evaluating a function depending either on a single selected metric or on each of the metrics and their associated weight values. Advantageously, this calculation is based on additional temporal information of the system that enables the sensing system to select a metric or assign weight values to one or more metrics in order to provide a concentration estimation in which inaccuracies caused by external factors are compensated.

According to various embodiments, a sensing system is implemented that includes a sensor and a processor. The sensing system is configured to calculate a concentration of a target analyte at the sensor by generating one or more event signals. The one or more event signals are generated according to a first signal obtained by the sensor. An event signal may include information about the temporal evolution of the sensing system. In various embodiments, the one or more event signals are obtained by applying a function to the first signal. In one embodiment, the one or more event signals include a derivative of the first signal. In another embodiment, the one or more event signals include an integral of the first signal.

A first weight value is calculated according to the first signal. Additional weight values are calculated corresponding to each of the event signals. The concentration of the target analyte at the sensor is calculated using the first weight value and additional weight values. The sensor is a resistive sensor in various embodiments and is a resistive gas sensor in some embodiments. In various embodiments, the sensor includes graphene. In one embodiment, the sensor is a reduced graphene oxide gas sensor.

The sensing systems described herein may advantageously utilize robust algorithms and detection mechanisms which can reliably cope with calibration inaccuracies, baseline drift, and other similar effects over a wide operating range. For example, the event signals generated by the sensing systems may add$_{res}$ s environmental instability of sensors by processing the incoming data to provide valuable information on sensor status and expected quality of estimates. The information provided by the event signals may further be used to optimize the estimation metrics and/or the signal model depending on a specific use case and/or operating point.

Considering the specific example of a chemical gas sensor, various metrics exist which may achieve different classification rates and concentration estimation accuracies in different situations. In some cases, a model such as a linear model may be incorporated in order to enable discrimination of target gas concentrations at a sensor. However, practical and environmental considerations may affect the various methods differently. For example, a processing algorithm implemented in a sensing system may have to decide whether a new concentration value is to be estimated, how long an observation interval should be, and which metric should be used in a given situation.

Embodiment sensing systems described herein may have the additional benefit of implementing concrete mechanisms which can be used in real products, such as mobile applications. These concrete mechanisms may overcome challenges related to limited and/or noisy data availability, imperfect initial calibration, partially unknown sensor status, stringent time requirements, modeling errors, and others. The sensing systems may adapt to specific operating scenarios and optimally make use of available samples and statistics.

Embodiments provided below describe various sensing systems and methods of operating sensing systems, and in particular, sensing systems that estimate an analyte concentration. The following description describes the embodiments. An embodiment method of estimating a concentration of a target analyte is described using FIG. 1. An embodiment sensing system is described using FIG. 2. Two embodiment schematic block diagrams of a sensing system are described using FIGS. 3 and 4. A qualitative graph of sensor resistance and the derivative of the sensor resistance versus time representing an example response of an embodiment sensing system is described using FIG. 5. An embodiment method of determining the status of a sensing system is described using FIG. 6. An embodiment schematic block diagram of a sensor coupled to a processing block is described using FIG. 7. Two embodiment schematic block diagrams of a metric selection block coupled to a concentration estimation block are described using FIGS. 8 and 9. An embodiment method of calculating a concentration of a target analyte is described using FIG. 10. A qualitative graph of sensor resistance and a dynamic moment versus time representing an example response of an embodiment sensing system is described using FIG. 11. Another embodiment method of determining the statues of a sensing system is described using FIG. 12. A graph of sensor resistance and the derivative of the sensor resistance versus time as detected by a sensor in an embodiment sensor system is described using FIG. 13. Yet another embodiment method of determining the status of a sensing system is described using FIG. 14. Two embodiment sensor devices are described using FIGS. 15 and 16.

FIG. 1 illustrates an example method of estimating a concentration of a target analyte by a sensing system in accordance with an embodiment of the invention.

Referring to FIG. 1, a method 100 of estimating a concentration of a target analyte by a sensing system includes the following steps. Step 101 includes obtaining sensing data. The sensing data may be obtained by one or more sensors included in the sensing system. For example, one or more sensors may be implemented in a sensing array of the sensing system. The sensing data may include an analog or a digital signal. In one embodiment, the sensing data obtained in step 101 includes resistance data from the one or more sensors. The step 101 of obtaining sensing data may refer to recording a single data point in an instant in time or may refer to gathering multiple data points over a period of time.

Step 102 of method 100 includes generating one or more event signals from the sensing data. The event signals may include values that are calculated using the sensing data. For example, the event signals may include a derivative, integral, energy vector, dynamic moment of the system, and the like. Multiple derivatives and/or integrals may be included as event signals. Similarly any complex function of the sensing data that is suitable to describe an aspect of the system may be included as an event signal. In various embodiments, the step 102 includes generating a single event signal. In one embodiment the single event signal is the derivative of the sensing data. In another embodiment, the single event signal is an integral of the sensing data. In still another embodiment, the single event signal is a dynamic moment of the system which uses the sensing data as an independent variable.

Step 103 of method 100 includes determining sensor status using the sensing data and the one or more event signals. For example, the sensing system may compare the sensing data and the event signals to predetermined values in order to determine the current status of the sensing system. Any suitable combination of the sensing data and event signals may be used in step 103. Possible states of the sensing system may include calibration, preparation, processing, recovery, and the like.

The previous status of the sensing system may be taken into account during step 103. For example, it may be determined that the sensing system must be in a preparation state immediately prior to being in a processing state. In this specific example, the sensing system may confirm that it is in the preparation state after detecting that the sensing data and/or event signals have met the requirements of the processing state. The sensing system may then update the current status of the sensing system to the processing state.

Step 104 of method 100 includes determining an optimal metric using the sensor status, sensing data, and the one or more event signals. During step 104, an operating region may be determined for the sensing system based on judicious combination of the sensing data and the event signals. For example, the operating region may be based on the presence of baseline drift and/or a large signal-to-noise ratio (SNR). The operating region may influence the determination of an optimal metric for use in estimating the concentration of a target analyte. For example, for a given operating region, weights may be calculated and assigned to the sensing data and the event signals to obtain an optimal metric.

Step 105 of method 100 includes estimating a concentration using the optimal metric determined in step 104. Step 105 may include calculating a concentration using the calculated weights of the optimal metric. After the concentration is estimated, the concentration may optionally be displayed in step 106 of method 100. The concentration may be displayed using any suitable display method such as a screen included in the sensing system. The concentration may alternatively be stored in a memory or sent to an external device or database.

Figure 2:
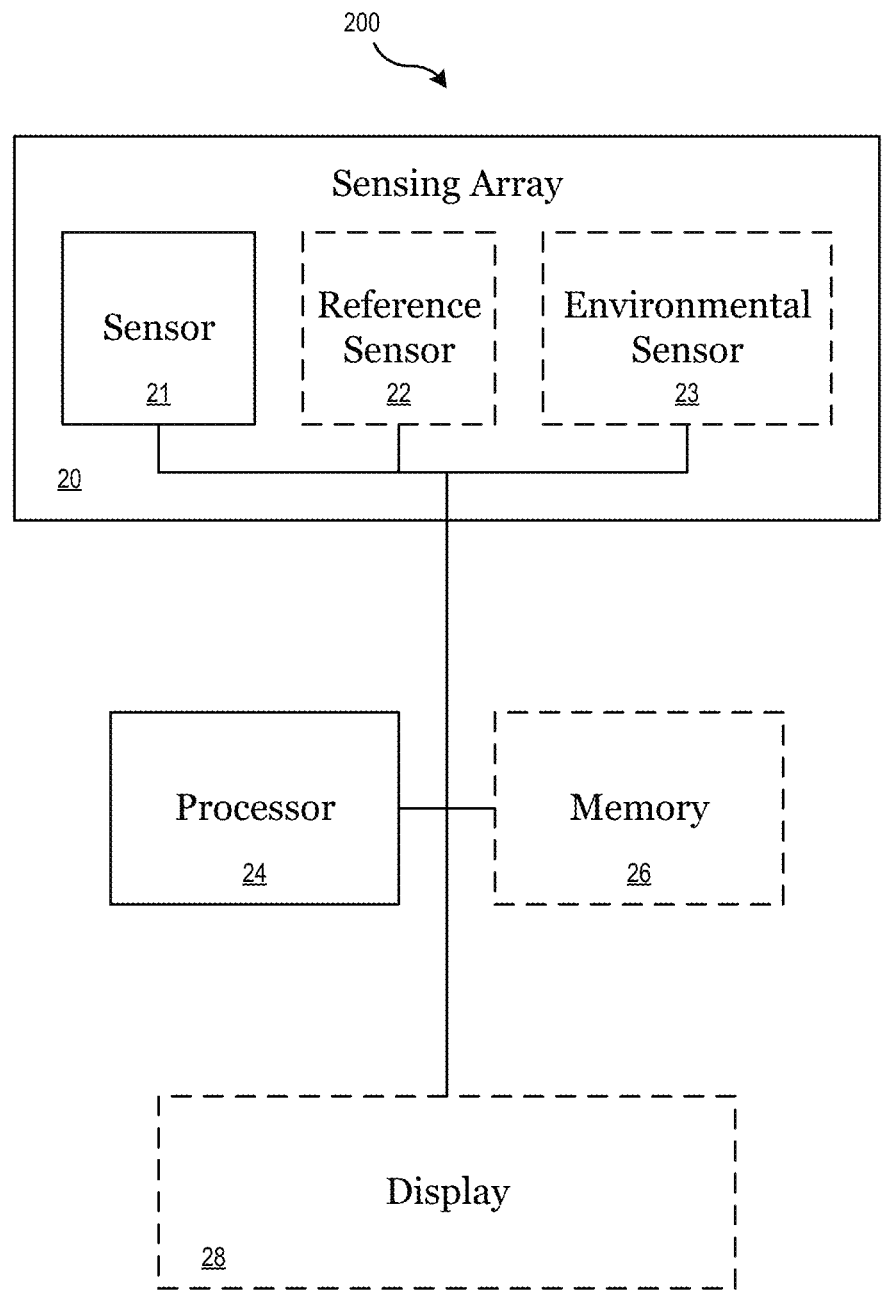
FIG. 2 illustrates an example sensing system including a sensor, a processor, and a memory in accordance with an embodiment of the invention.

FIG. 2 illustrates an example sensing system including a sensor, a processor, and a memory in accordance with an embodiment of the invention. The sensing system of FIG. 2 may be configured to perform the method described herein such as the method 100 of FIG. 1, for example.

Referring to FIG. 2, a sensing system 200 includes a sensing array 20. The sensing array 20 may be configured to perform step 101 of method 100. The sensing array 20 includes one or more sensors 21. The sensors 21 are configured to respond to the presence of a target analyte. In one embodiment, the sensing array 20 includes a single sensor 21. In another embodiment, the sensing array 20 includes multiple sensors 21 arranged in an array. Sensors 21 included in the sensing array 20 may be identical or may include multiple types of sensors 21.

The sensing array 20 may also optionally include a reference sensor 22 and/or and environmental sensor 23. The reference sensor 22 may be used to determine appropriate baseline values for the sensing system 200 given different ambient environments. The environmental sensor 23 may be included to measure environmental conditions such as temperature or humidity. The measured environmental conditions may be used to improve the accuracy of the sensing system 200.

A processor 24 may also be included in sensing system 200. The processor 24 may be operatively coupled to the sensing array 20. The processor 24 may be an application-specific integrated circuit (ASIC), a field-programmable gate array (FPGA), or a general purpose processor coupled to an optional memory 26 included in sensing system 200. The processor 24 may be configured to perform one or more of steps 102-105 of method 100. Alternatively, any of steps 102-105 may be performed externally by a computer that is connected to the sensing system such as a desktop computer, laptop computer, server, tablet computer, smart phone, and the like.

The memory 26 may be operatively coupled to the processor 24 and/or the sensing array 20 and may be used to store information obtained by measuring and processing the sensing data. The memory 26 may also be used to store computer instructions that, when executed by processor 24, may perform steps 102-105 among others. Memory 26 may be a non-volatile computer-readable storage medium such as a computer hard drive, random access memory, and the like.

The sensing system 200 may also include and optional display 28. The display 28 may be operatively coupled to one or more of the sensing array 20, processor 24, and the memory 26. For example, the display 28 may be a screen such as a liquid-crystal display (LCD) screen, light emitting diode (LED) screen, and the like. The display 28 may be configured to perform step 106 of method 100.

Figure 3:
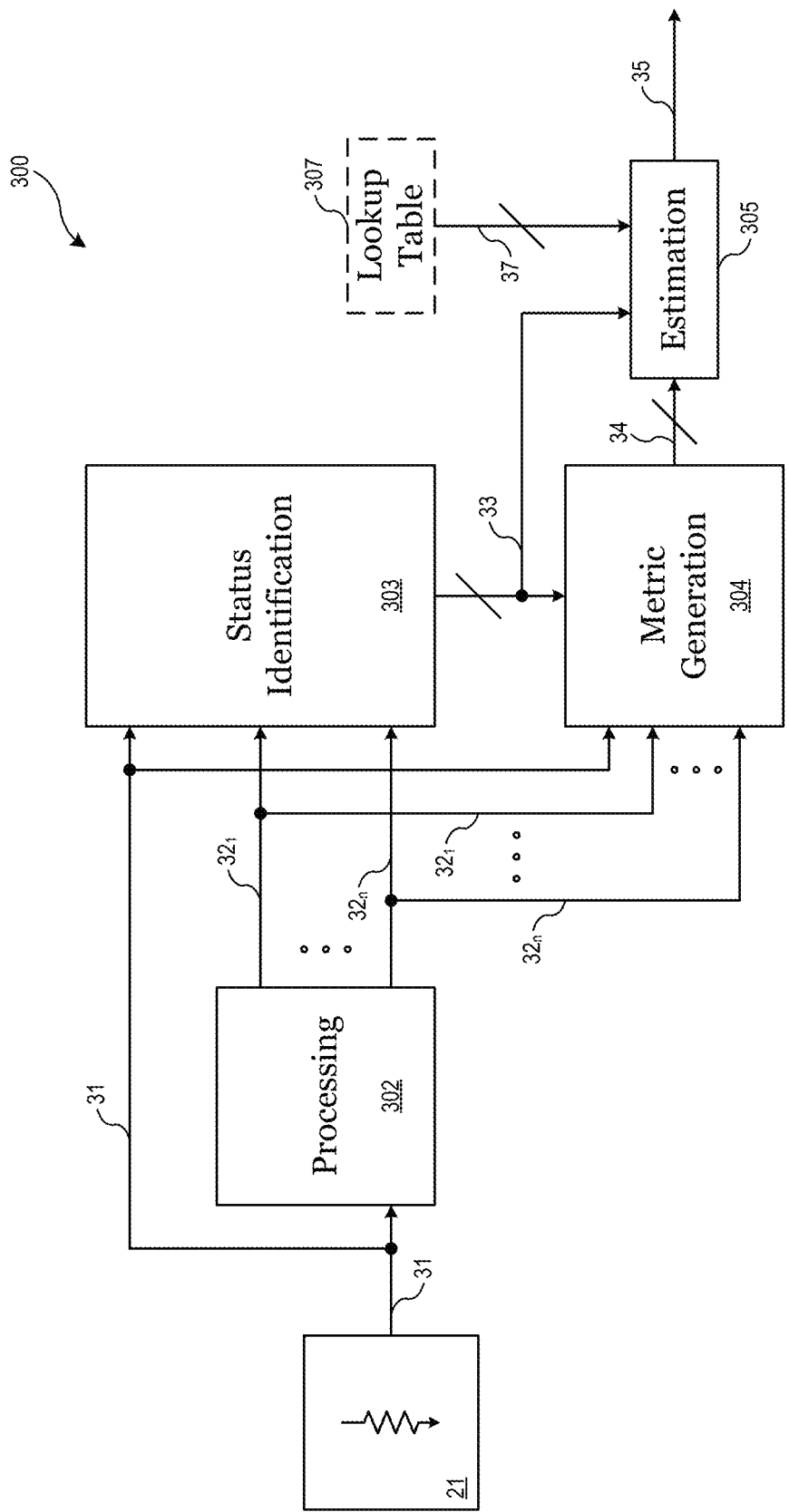
FIG. 3 illustrates an example schematic block diagram of a sensing system configured to estimate a concentration of a target analyte detected at a sensor in accordance with an embodiment of the invention.

FIG. 3 illustrates an example schematic block diagram of a sensing system configured to estimate a concentration of a target analyte detected at a sensor in accordance with an embodiment of the invention. The sensing system of FIG. 3 may be a specific implementation of other sensing systems described herein such as the sensing system 200 of FIG. 2, for example.

Referring to FIG. 3, a sensing system 300 includes a sensor 21 coupled to a processing block 302 and a status identification block 303. The sensor 21 generates sensing data 31 in response to the presence of a detectable concentration of a target analyte at the sensor 21. In various embodiments, the sensor 21 is a gas sensor. In some embodiments, the sensor 21 is a resistive sensor. In one embodiment the sensor 21 is a resistive gas sensor. The sensor 21 may include a functionalized surface configured to interact with target analytes. In various embodiments sensor 21 includes graphene and includes reduced graphene oxide in one embodiment.

Sensor 21 may be a sensing array in some embodiments. The sensing array may be configured to generate multiple sensing data signals which may then be processed by processing block 302. The multiple sensing data signals may be processed in parallel or averaged for use by the sensing system 300. In some cases the multiple sensing data signals may be combined to generate an event signal such as an energy vector.

The sensing data 31 may be sent to the processing block 302 and the status identification block 303. The processing block 302 is configured to generate one or more event signals $32_1$-$32n$ using the sensing data 31 received from sensor 21. The event signals $32_1$-$32n$ may be functions of the sensing data 31. For example, the event signals $32_1$-$32n$ may include various signals generated from sensing data 21 such as derivatives, integrals, energy vectors, and dynamic moments of the system. The status identification block 303 may also receive the event signals $32_1$-$32n$ from processing block 302. In various embodiments, the event signals $32_1$-$32n$ include information of the temporal evolution of the sensing system.

Status identification block 303 is configured to use the received sensing data 31 and the event signals $32_1$-$32n$ to determine a sensor status 33 of the sensing system 300. The sensor status 33 is sent to a metric generation block 304 and an estimation block 305. Sensing data 31 from sensor 21 and the event signals $32_1$-$32n$ from processing block 302 are also sent to the metric generation block 304. The metric generation block 304 is configured to generate one or more metrics and determine an optimal metric 34 using the sensing data 31, event signals $32_1$-$32_n$, and sensor status 33.

The optimal metric 34 is then sent to the estimation block 305. The estimation block 305 is configured to estimate a concentration 35 of the target analyte that generated the sensing data 31 at the sensor 21. For example, the concentration 35 may be estimated by calculating a concentration value using weights determined according to the optimal metric 34. In this way, the sensing system 300 parameterizes the estimation algorithm using the sensing data 31 and the event signals $32_1$-$32_n$. Some or all direct calculation may be avoided by using an optional lookup table 307 coupled to the estimation block 305. If a lookup table 307 is included in sensing system 300, then a lookup table input/output (I/O) 37 couples the estimation block 305 to lookup table 307. The lookup table 307 may be used to estimate the concentration 35 of the target analyte by looking up the sensing data 31 and/or event signals $32_1$-$32_n$ in a table of concentration values.

It should also be noted that any equations and associated calculations as described herein may be accomplished using any suitable method including, but not limited to, direct digital calculation, lookup tables, logical operations, and analog signal processing. Additionally, each of the methods may be used in any functional block of an embodiment sensing system. For example, a lookup table may be included in or be coupled to processing block 302. Alternatively, some or all of the processing performed in processing block 302 may be analog transformations of received signals. As still another alternative, some or all of the processing in processing block 302 may be performed digitally. Similar variations apply to other functional blocks described in this and other embodiments.

Figure 4:
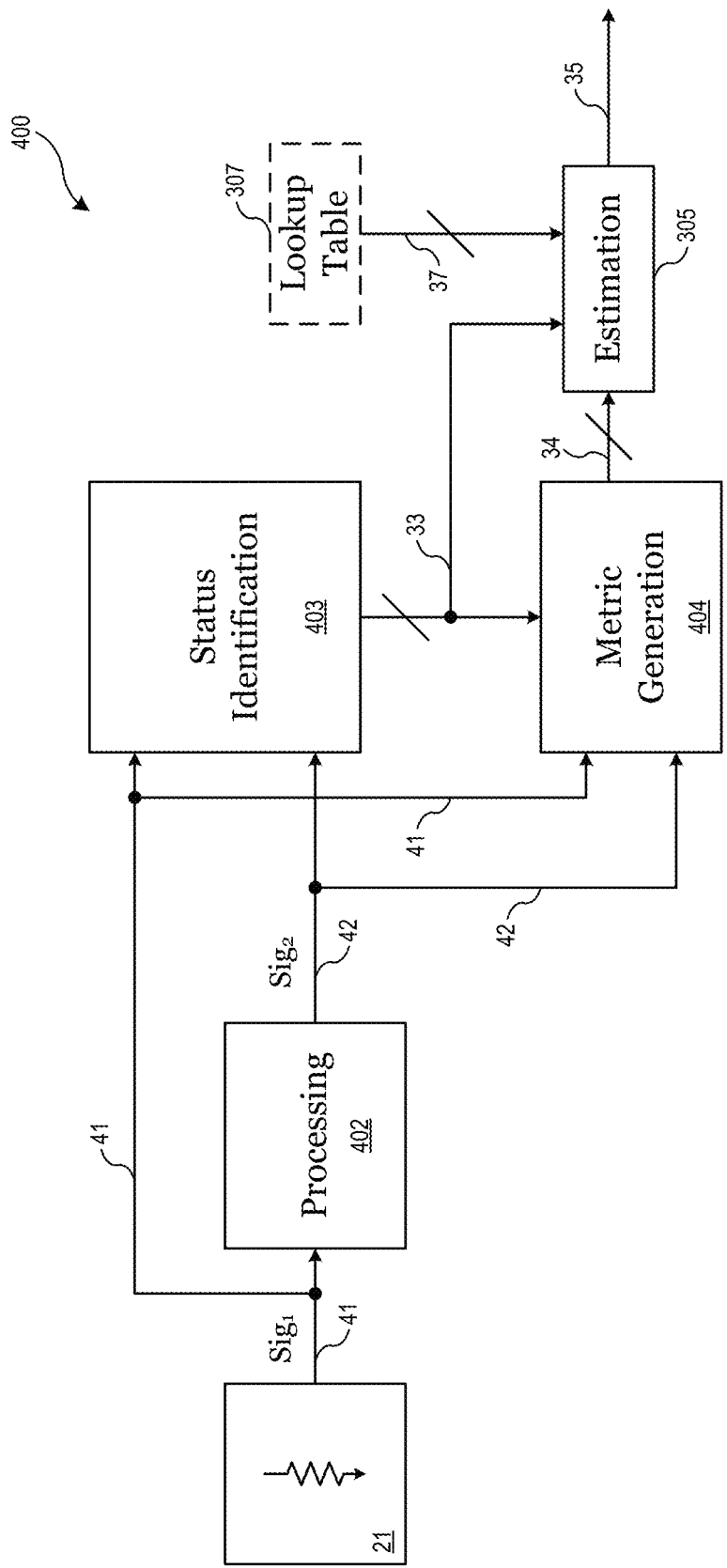
FIG. 4 illustrates another example schematic block diagram of a sensing system configured to estimate a concentration of a target analyte detected at a sensor in accordance with an embodiment of the invention.

FIG. 4 illustrates another example schematic block diagram of a sensing system configured to estimate a concentration of a target analyte detected at a sensor in accordance with an embodiment of the invention. The sensing system of FIG. 4 may be a specific implementation of other sensing systems described herein such as the sensing system 300 of FIG. 3, for example. All similarly labeled elements are as previously described.

Referring to FIG. 4, a sensing system 400 includes a sensor 21 coupled to a processing block 402 and a status identification block 403. The processing block 402 may be a specific implementation of processing block 302 of FIG. 3 that receives a signal $Sig_1$ 41 and generates a single event signal $Sig_2$ 42. In various embodiments, $Sig_1$ 41 is a resistance measured at sensor 21. In one embodiment, $Sig_2$ 42 is a derivative of $Sig_1$ 41. In another embodiment, $Sig_2$ 42 is an integral of $Sig_1$ 41. In still another embodiment, $Sig_2$ 42 is a dynamic moment of the system calculated using $Sig_1$ 41. In yet another embodiment, $Sig_2$ 42 is an energy vector of the system calculated using multiple signals obtained by a sensing array optionally included in place of sensor 21.

The status identification block 403 is configured to receive $Sig_1$ 41 and $Sig_2$ 42 and determine a sensor status 33 of the sensing system 400. For example, status identification block 403 may be a specific implementation of status identification block 303 of FIG. 3. Similarly, metric generation block 404 may be a specific implementation of metric generation block 304 and may be configured to receive $Sig_1$ 41 and $Sig_2$ 42, generate one or more metrics, and determine an optimal metric 34. In one embodiment, $Sig_1$ 41 is a direct measurement obtained from one or more sensors of the sensing system while $Sig_2$ 42 includes information about the temporal evolution of the sensing system.

Status identification block 403 and metric generation block 404 are coupled to estimation block 305. A lookup table 307 is optionally coupled to estimation block 305 using lookup table I/O 37. Estimation block 305 is configured to estimate concentration 35 and is as previously described.

Figure 5:
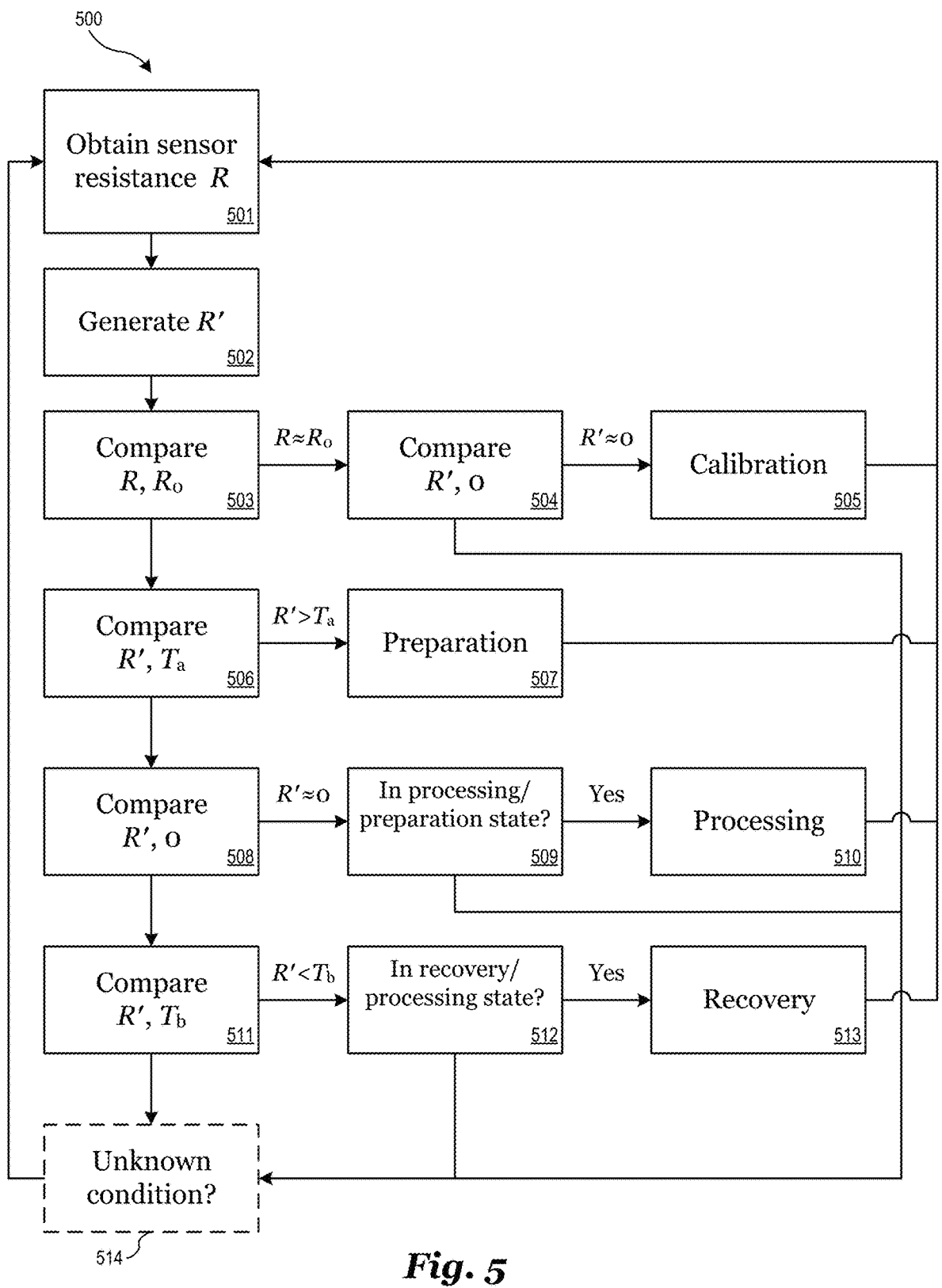
FIG. 5 illustrates an example method of determining the status of a sensing system using sensor resistance and the derivative of the sensor resistance in accordance with an embodiment of the invention.

FIG. 5 illustrates an example method of determining the status of a sensing system using sensor resistance and the derivative of the sensor resistance in accordance with an embodiment of the invention. The method of FIG. 5 may be performed by a sensing system as described in other embodiments such as the sensing system 400 of FIG. 4, for example.

Referring to FIG. 5, a method 500 of determining the status of a sensing system includes the following steps. Step 501 includes obtaining a sensor resistance R. The sensor resistance R may refer to a single value or a collection of data points obtained during an observation window. In some cases R may also refer to a collection of resistances obtained, for example, from a sensing array. The derivative of the resistance R' is generated using R in step 502. It should be noted that the derivative R' is taken with respect to time and is the slope of the resistance curve R(t).

After R and R' have been obtained, the sensing system performs a series of comparisons to determine the status of the sensing system based on R and R'. For example, the set of possible statuses for the sensing system may include a calibration interval, a preparation interval, a processing interval, and a recovery interval, among others. The reference to an interval when describing a status of the sensing system may refer to a period of time during which specific criteria involving R and R' are met. The length of a given interval may depend on the environment, type of sensor, and specific target analyte. For example, an interval may extend for several iterations of method 500. In contrast, the status of the sensing system may change quickly resulting in an interval existing for only a single iteration of method 500.

The sensing system may also maintain an active state for comparison purposes. As an example, the sensing system may determine that the system is in a preparation interval and set the state of the system to the preparation state. Subsequent steps of method 500 may then check the state of the sensing system and determine that the sensing system is operating in the preparation state. In various embodiments, each status interval of the sensing system has an associated system state. Alternatively, not all of the status intervals have an associated system state. For example, a recovery interval may or may not have an associated recovery state depending on specific implementations of method 500.

Still referring to FIG. 5, the sensing system compares R to a baseline resistance value $R_0$ in step 503. The baseline resistance $R_0$ may be predetermined through initial calibration of the sensing system in a controlled environment. In some cases, the baseline resistance $R_0$ may be adjusted to compensate for baseline drift. If the sensing system determines that the resistance is substantially equal to the baseline resistance value ($R \approx R_0$), then the sensing system compares R' to zero in step 504. The sensing system then determines that the system is the calibration interval if R' is substantially zero ($R' \approx 0$) in step 505.

The sensing system may optionally enter a calibration state in step 505 which may include various functions such as detecting the presence of baseline drift within the sensing system and quantifying the noise level within the sensing signal. The baseline drift and the noise level may be used to improve the accuracy of future concentration estimations made by the sensing system. For example, baseline drift may be corrected and/or appropriate metrics may be selected/combined during concentration estimation. Various states of the sensing system, such as the calibration state, may be triggered by event signals that are sent between functional blocks within the sensing system. The states of the sensing system may also be tracked in other ways such as using registers, as an example.

If R is determined not to be substantially equal to $R_0$ in step 503, then the sensing system compares R' to a threshold slope value $T_a$ in step 506. The threshold slope value $T_a$ may be predetermined based on the specific implementation of the sensing system and interaction details of a given target analyte. In step 507, the sensing system determines that the system is in the preparation interval if the slope of the resistance is greater than the threshold slope value ($R'>T_a$) in step 506. The preparation interval may correspond to a period of time when the sensing system is detecting an increasing resistance signal. For example, a preparation interval may be the time period between an interval with no detected concentration and a substantially stable period of non-zero concentration. In addition to identifying the preparation interval, the sensing system may also enter a preparation state in step 507.

In step 506, if R' is determined not to be greater than $T_a$ then the sensing system compares R' to zero. The sensing system then checks if the system is in the preparation state or the processing state in step 509 if R' is determined to be substantially equal to zero in step 509. After determining that the system is in currently in the preparation state or the processing state, the sensing system determines that R and R' indicate that the status of the system is the processing interval in step 510. During step 510 the sensing system may also enter a processing state which may include various functions such as generating metrics, selecting metrics, determining an optimal metric, and estimating a concentration of a target analyte, among others.

If R' is determined to not be substantially equal to zero in step 508, then the sensing system compares R' to another threshold slope value $T_b$ in step 511. As with previously described predetermined values, $T_b$ may be based on a specific implementation of the sensing system and interaction details of a given target analyte. If the sensing system determines that the slope of the resistance is less than the threshold slope value ($R'<T_b$) then the sensing system checks if the system is in the processing state or the recovery state in step 512. After determining that the system is in the processing state or the recovery state, the sensing system identifies the status of the system as the recovery interval in step 513.

The length of each processing interval may define an observation window. For example, the observation window may be a period of time during which data is obtained to directly estimate a concentration of a target analyte by the sensing system. During an observation window, the sensing system may further process the sensing data by averaging samples, smoothing data, adding/removing outliers, and filtering the data to reduce signal noise.

As with previous steps where a status is successfully identified, the sensing system may also enter a recovery state in step 513. In some embodiments, when the sensing system reaches step 509 of method 500, the sensing system may also check to see if the system is in the recovery state in addition to checking for the preparation state. The sensing system may then proceed to step 510 if the system is in the recovery state. This may allow estimation of concentrations when the concentration of the target analyte does not return to zero in between sensing events.

At various steps in method 500, it may be possible for the sensing system to determine that R, R', and the operating state of the system do not fully meet the criteria of any of the predetermined statuses. In this case, the system may either maintain the current state of the system without making a positive identification and return to step 501 or the exception may be handled on a case by case basis in a step 514. For example, in step 504, it may be determined that R' does not substantially equal zero. However, there may be no identifiable status corresponding to $R \approx R_0$ and $R' \approx 0$. In this case, the exception may be handled in an optional step 514 before the sensing system returns to step 501 to evaluate another resistance and resistance derivative.

As shown in FIG. 5, other steps may lead to step 514 including steps 509, 512, and 514. It should also be noted that the sensing system may return to step 501 after any positive identification of the status of the sensing system. For example, steps 505, 507, 510, and 513 may also lead to step 501 of method 500. However, since these steps result in a status being identified, optional step 514 is bypassed after these steps.

For the purposes of this and other embodiments described herein, a sensing system may determine that a value is substantially equal to another value by using a predetermined tolerance or by virtue of limitations of the sensing system. For example, in the above described step 503, R may be determined to be substantially equal to $R_0$ if $(0.95)R_0 < R < (1.05)R_0$ which may be considered a ±5% tolerance. Other tolerance values may be used and may be based on rounded values rather than percentages. The interpretation of substantially equal to may vary based on specific implementation as will be apparent to those or ordinary skill in the art.

Figure 6:
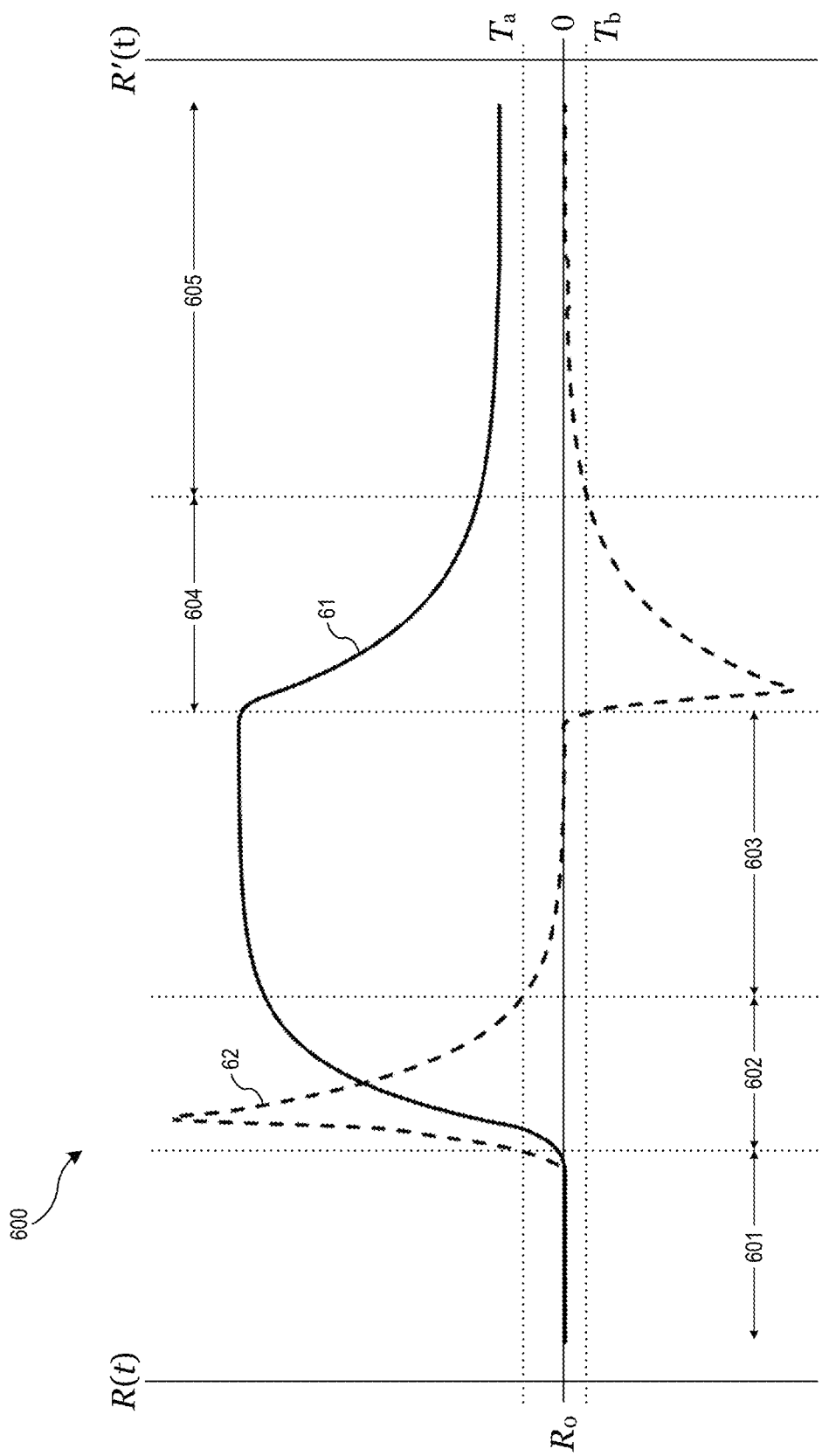
FIG. 6 illustrates a qualitative graph of sensor resistance versus time as detected by a sensing system and the derivative of the sensor resistance versus time as generated by the sensing system in accordance with an embodiment of the invention.

FIG. 6 illustrates a qualitative graph of sensor resistance versus time as detected by a sensing system and the derivative of the sensor resistance versus time as generated by the sensing system in accordance with an embodiment of the invention. The graph of FIG. 6 may be a representative response of a sensing system as described in other embodiments such as sensing system 400 of FIG. 4, for example.

Referring to FIG. 6, the sensor resistance R(t) 61 and the slope of the resistance R'(t) 62 are plotted as a function of time t in graph 600. The curves R(t) and R'(t) may be used to determine the status of the sensing system as previously described in method 500 of FIG. 5 as an example. The slope of the resistance may be obtained by determining the derivative of the resistance with respect to time. As seen in graph 600, the sensor resistance 61 begins at $R_0$ and the slope of the resistance 62 begins at zero in interval 601. This corresponds to the calibration interval as described in method 500. Environmental conditions such as baseline drift and noise level may easily be evaluated during this interval since there is no detected change in the resistance from the baseline value of $R_0$.

During interval 602, the sensor resistance 61 and the slope of the resistance 62 increase. Specifically, R(t) is greater than $R_0$ and R'(t) is greater than $T_a$ during interval 602. These conditions correspond with the preparation interval of method 500. The increase of the slope of the resistance 62 may indicate that a target analyte is reaching the sensor. As the concentration of the target analyte at the sensor stabilizes, the slope of the resistance 62 decreases creating a peak during interval 602.

During the next interval 603, the slope of the resistance 62 decreases until R'(t) is less than $T_a$. This, in conjunction with the condition that the preceding interval is a preparation interval, indicates that the conditions are met for the processing interval of method 500. As can be seen in graph 600, the resistance 61 is stable at an elevated value above $R_0$ during the interval 603. This may allow a stable measurement to be obtained and an accurate concentration estimate to be made.

When the resistance 61 begins to decrease, the system enters interval 604. In interval 604, the slope of the resistance 62 is negative and less than $T_b$ while the resistance 61 is decreasing. As can be seen in method 500, this corresponds to the recovery interval as long as the preceding interval is a processing interval. During this interval, the sensing system may stop processing the incoming sensing data.

In interval 605, the slope of the resistance 62 meets the criteria for a calibration interval or a processing interval. However, the preceding interval 604 is a recovery interval as described above. In the scenario of interval 605, the sensing system may determine that the resistance 61 is substantially equal to $R_0$ because the resistance value R is with a predetermined tolerance range of $R_0$. In this case, interval 605 would be determined to be a calibration interval. Alternatively, the sensing system may determine that the resistance 61 is high enough above $R_0$ to constitute a sensing event. The sensing event may represent the presence of a lower concentration of the target analyte at the sensor than that of interval 603. In this case, interval 605 may be determined to be a processing interval.

As another alternative, the sensing system may determine that the interval 605 represents an unknown status of the sensing system. For example, the resistance value R may be too low to be considered a sensing event, but may be too high to be substantially equal to $R_0$. This may be caused by baseline drift during a prolonged processing interval, changes in the environment such as temperature or humidity, the presence of species other than the target analyte in the environment, and others. The sensing system may be configured to handle this exception on a case by case basis. For example, in one embodiment, the sensing system handles the exception in a step 514 of method 500.

It should be noted that the sign of $T_a$ and $T_b$ may depend on specific details of the target analyte. In the method 500 of FIG. 5 and the graph 600 of FIG. 6, the sensing system is configured to exhibit an increase in resistance in response to the presence of a target analyte. In this scenario, $T_a$ is positive while $T_b$ is negative. However, it is possible for the sensing system to be configured to exhibit a decrease in resistance in response to the presence of a target analyte. In this alternative scenario, $T_a$ would be negative while $T_b$ would be positive and the corresponding comparisons in step 506 and step 511 of method 500, for example, would be reversed to be $R'<T_a$ and $R'>T_b$ respectively.

Figure 7:
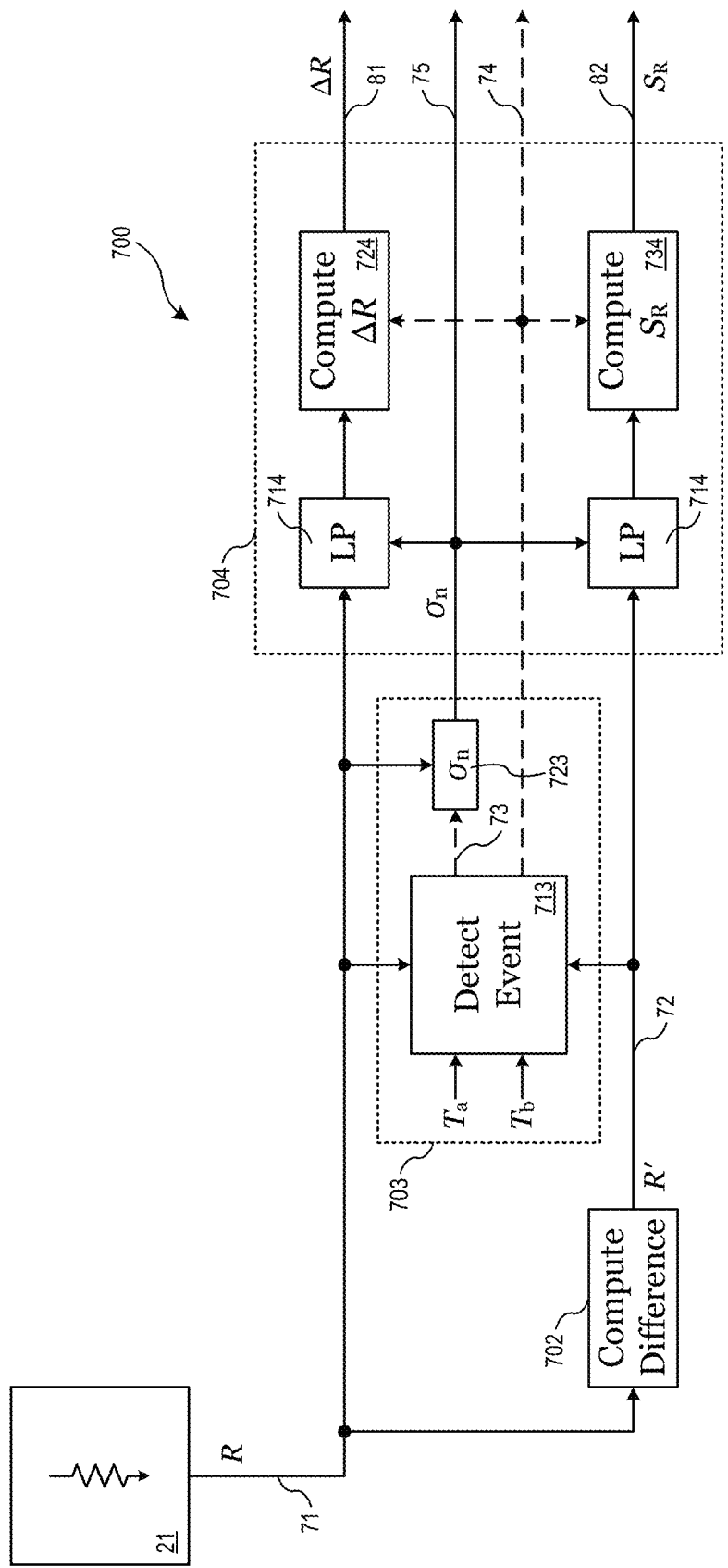
FIG. 7 illustrates an example schematic block diagram of a sensor coupled to a processing block configured to a sensor resistance, the derivative of the sensor resistance, and a status signal in accordance with an embodiment of the invention.

FIG. 7 illustrates an example schematic block diagram of a sensor coupled to a processing block configured to a sensor resistance, the derivative of the sensor resistance, and a status signal in accordance with an embodiment of the invention. The sensing system of FIG. 7 may be a specific implementation of other sensing systems or portions of other sensing systems described herein such as the sensing system 400 of FIG. 4, for example.

Referring to FIG. 7, a sensing system 700 includes a sensor 21 coupled to a processing block 702, a status identification block 703, and a metric generation block 704. A resistance R signal 71 is sent from sensor 21 to processing block 702, status identification block 703, and metric generation block 704. Processing block 702 may be a specific implementation of the processing block 402 of FIG. 4 which receives the resistance R signal 71 and generates a slope of the resistance R' signal 72 by computing the difference between adjacent resistance data points. Alternatively, the slope of the resistance R' signal 72 may be calculated using any suitable method of calculating a derivative.

The slope of the resistance R' signal 72 is sent to status identification block 703 and metric generation block 704 using respective connections. The status identification block 703 includes an event detection block 713 that receives a first threshold slope value $T_a$ and a second threshold slope value $T_b$ in addition to R and R'. Alternatively, event detection block 713 may store $T_a$ and $T_b$ internally rather than receiving the values as inputs. The event detection block 713 uses R, R', $T_a$, and $T_b$ to detect events corresponding to the status of the sensing system. For example, if the event detection block 713 determines that the system is in a calibration interval, then a trigger signal 73 may be sent to a noise variance estimation block 723 which is configured to estimate the variance of the background noise $\sigma_n$ from the received resistance R signal 71. For example, the noise variance $\sigma_n$ may be the standard deviation of the received resistance R signal 71 over a period of time during a calibration interval. Alternatively, the noise variance $\sigma_n$ may be the variance (square of the standard deviation) of the received resistance R signal 71 over a period of time during a calibration interval. The noise variance estimation block 723 then outputs a variance $\sigma_n$ signal 75.

The variance $\sigma_n$ signal 75 may be received by low pass filters 714 included in the metric generation block 704. The noise variance an may be used to determine a cutoff frequency or a bandwidth for the low pass filters 714. In one embodiment, the low pass filters 714 may be used to filter the resistance R signal 71 and the slope of the resistance R' signal 72. In other embodiments, only one or neither of the signals 71 and 72 may be filtered.

The event detection block may detect that the system is in a preparation interval, processing interval, or a recovery interval. For these cases, the sensing system may output a trigger signal 74. The trigger signal 74 may trigger events within the metric generation block 704 as well as other blocks not shown in FIG. 7. For example, trigger signal 74 may be received by a resistance variation ΔR computation block 724 and a maximum slope $S_R$ computation block 734.

The trigger signal 74 may trigger ΔR computation block 724 to compute ΔR for a particular time period. In one embodiment ΔR is computed using the equation $\Delta R = R - R_0$. In another embodiment, ΔR is computed using the equation $\Delta R = R/R_0$. In one embodiment, ΔR may be calculated by taking the difference between the measured resistance values at the beginning and end of a preparation interval. The resistance variation ΔR may be computed for the specific time period of the preparation interval in one embodiment. After computing ΔR the ΔR computation block 724 may output a ΔR signal 81.

In addition to triggering the computation of ΔR, trigger signal 74 may also trigger maximum slope $S_R$ computation block 734 to compute $S_R$ for a particular time period. For example, $S_R$ computation block 734 may compute $S_R$ using the equation $S_R = \max_{t_1, t_2}(R')$. In one embodiment, the time interval from $t_1$ to $t_2$ is the preparation interval. After computing $S_R$, the $S_R$ computation block 734 may output a $S_R$ signal 82. The maximum slope $S_R$ may be the peak of the R' curve during the preparation interval.

Figure 8:
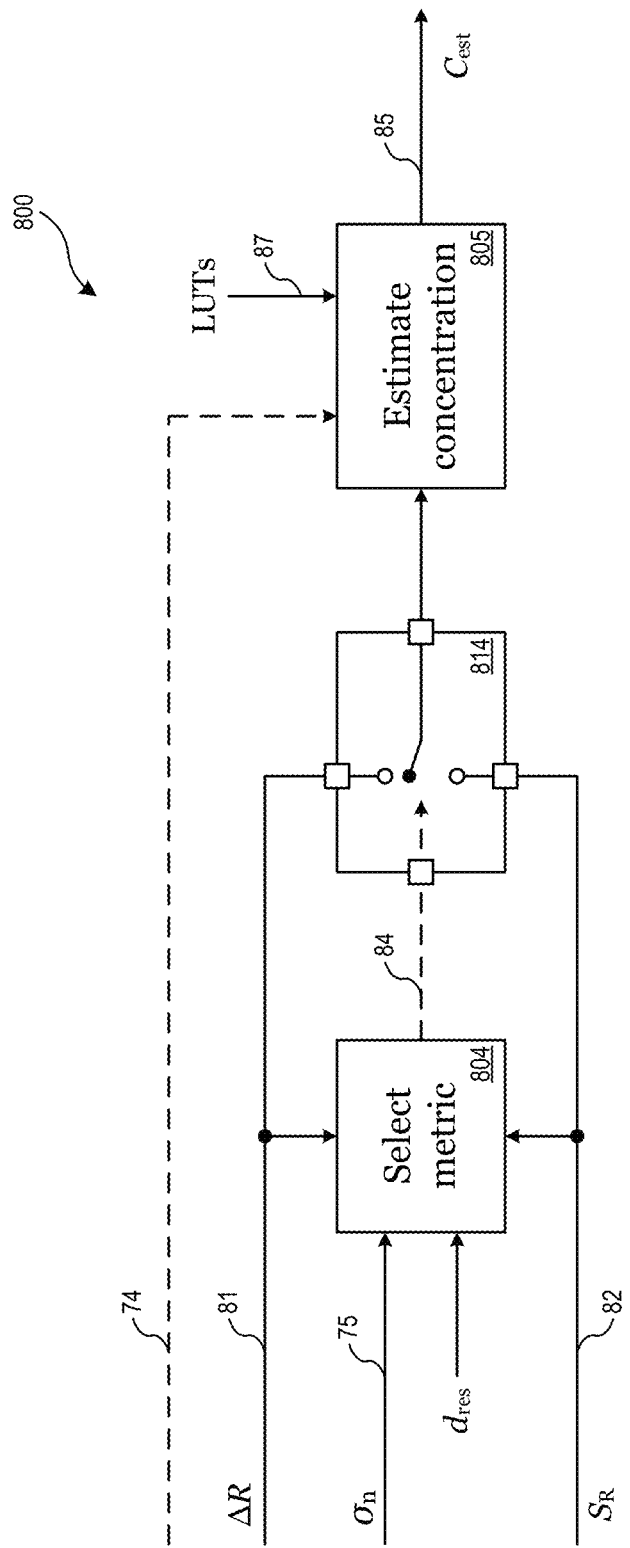
FIG. 8 illustrates an example schematic block diagram of a metric selection block coupled to a concentration estimation block configured to estimate a concentration of a target analyte detected at a sensor using sensor resistance and the derivative of the sensor resistance in accordance with an embodiment of the invention.

FIG. 8 illustrates an example schematic block diagram of a metric selection block coupled to a concentration estimation block configured to estimate a concentration of a target analyte detected at a sensor using sensor resistance and the derivative of the sensor resistance in accordance with an embodiment of the invention. The sensing system of FIG. 8 may be a specific implementation of other sensing systems or portions of other sensing systems described herein such as the sensing system 400 of FIG. 4, for example.

Referring to FIG. 8, a sensing system 800 includes a resistance variation ΔR signal 81 and a maximum slope $S_R$ signal 82 received at a metric selection block 804 and a switch 814. The metric selection block 804 may receive a noise variance an signal 75 and/or a residual drift value $d_{res}$. The residual drift value $d_{res}$ may be a representative value that quantifies the amount of baseline drift detected by the sensing system. For example, $d_{res}$ may be a change in resistance over a calibration interval. Alternatively, $d_{res}$ may be an average slope of the resistance over a calibration interval. Other specific definitions of the residual drift $d_{res}$ are possible and may be apparent to one or ordinary skill in the art.

Other values may be passed to metric selection block 804. In one embodiment, a signal-to-noise ratio SNR may also be received at metric selection block 804. The signal-to-noise ratio SNR may be computed by another functional block. In one embodiment, SNR is computed by a processing block such as processing block 702 of FIG. 7, as an example. Alternatively, SNR is computed in the metric selection block 804 or in a dedicated SNR computation block that passes the SNR value to the metric selection block 804. The SNR may be calculated using the equation $SNR = \Delta R/\sigma_n$. For example, ΔR may be calculated using a measured resistance R and a predetermined or calculated baseline resistance value $R_0$ as previously described. The noise variance $\sigma_n$ may be calculated using a measured resistance R that is measured during a period of negligible concentration of the target analyte at the sensor. Such a period may be, for example, a calibration interval during which one or more metrics are below predetermined threshold values.

The metric selection block 804 is configured to select a metric based on received and/or internally computed values such as $\sigma_n$, $d_{res}$, and SNR. For example, if the sensing system experiences a large baseline drift, then the ΔR metric may deliver highly biased concentration estimations. In this case, the metric selection block 804 may select $S_R$ as the metric. Selecting SR as a metric may be advantageous in order to use a metric that is less affected by baseline drift. As another example, the sensing system may experience large noise levels within the sensing data. In this case, the metric selection block 804 may select ΔR as the metric. Selecting ΔR as a metric may be advantageous in order to use a metric that is robust against noise.

After the metric selection block 804 selects the appropriate metric, a selection signal 84 may be sent to the switch 84 which passes the appropriate signal to an estimation block 805. The estimation block 805 may be triggered to estimate a concentration by a trigger signal 74 which may be generated by an event detection block such as event detection block 713 of FIG. 7, for example. As described previously, the estimation block 805 may also use an LUT I/O 87 to reduce the computational requirements of estimating the concentration. After estimating the concentration, the estimation block 805 may output an estimated concentration $C_{est}$ signal 85.

Figure 9:
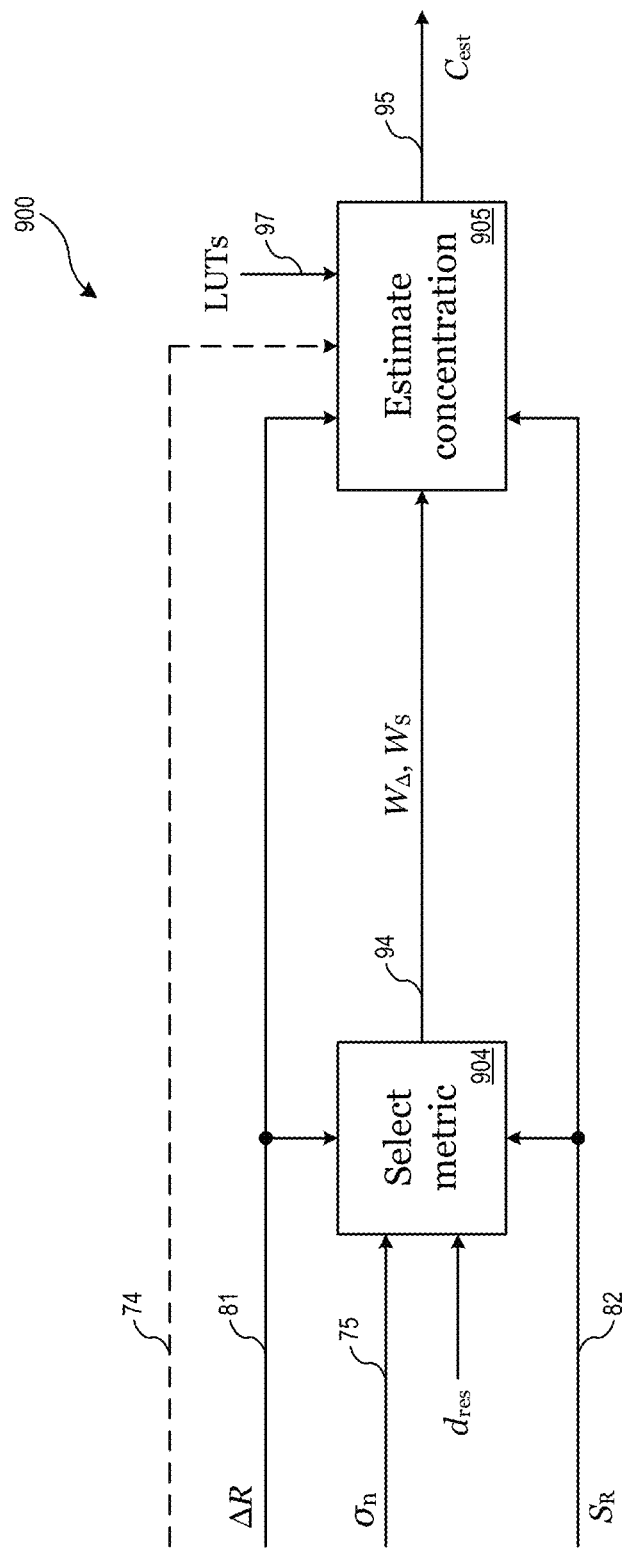
FIG. 9 illustrates another example schematic block diagram of a metric selection block coupled to a concentration estimation block configured to estimate a concentration of a target analyte detected at a sensor using sensor resistance and the derivative of the sensor resistance in accordance with an embodiment of the invention.

FIG. 9 illustrates another example schematic block diagram of a metric selection block coupled to a concentration estimation block configured to estimate a concentration of a target analyte detected at a sensor using sensor resistance and the derivative of the sensor resistance in accordance with an embodiment of the invention. The sensing system of FIG. 9 may be a specific implementation of other sensing systems or portions of other sensing systems described herein such as the sensing system 400 of FIG. 4, for example.

Referring to FIG. 9, the sensing system 900 is similar to the sensing system 800 of FIG. 8 except that a metric selection block 904 may compute weights for individual metrics ($W_\Delta$ and $W_S$) in addition to selecting a single metric. For example, metric weight $W_\Delta$, $W_S$ signal 94 may be passed to an estimation block 905 without the use of a switch. In cases where the metric selection block 904 selects a single metric, one of the weights may be set to a value of one while the other is set to zero. In cases where the metric selection block 904 selects a combination of metrics, each weight may be set to a value between zero and one. The estimation block uses the $W_\Delta$, $W_S$ signal 94 in addition to the $\Delta R$ signal 81 and $S_R$ signal 82 to generate an estimated concentration $C_{est}$ signal 95. As with other embodiments, the estimation block 905 may also make use of a LUT I/O 97 to reduce the number of required calculations.

Figure 10:
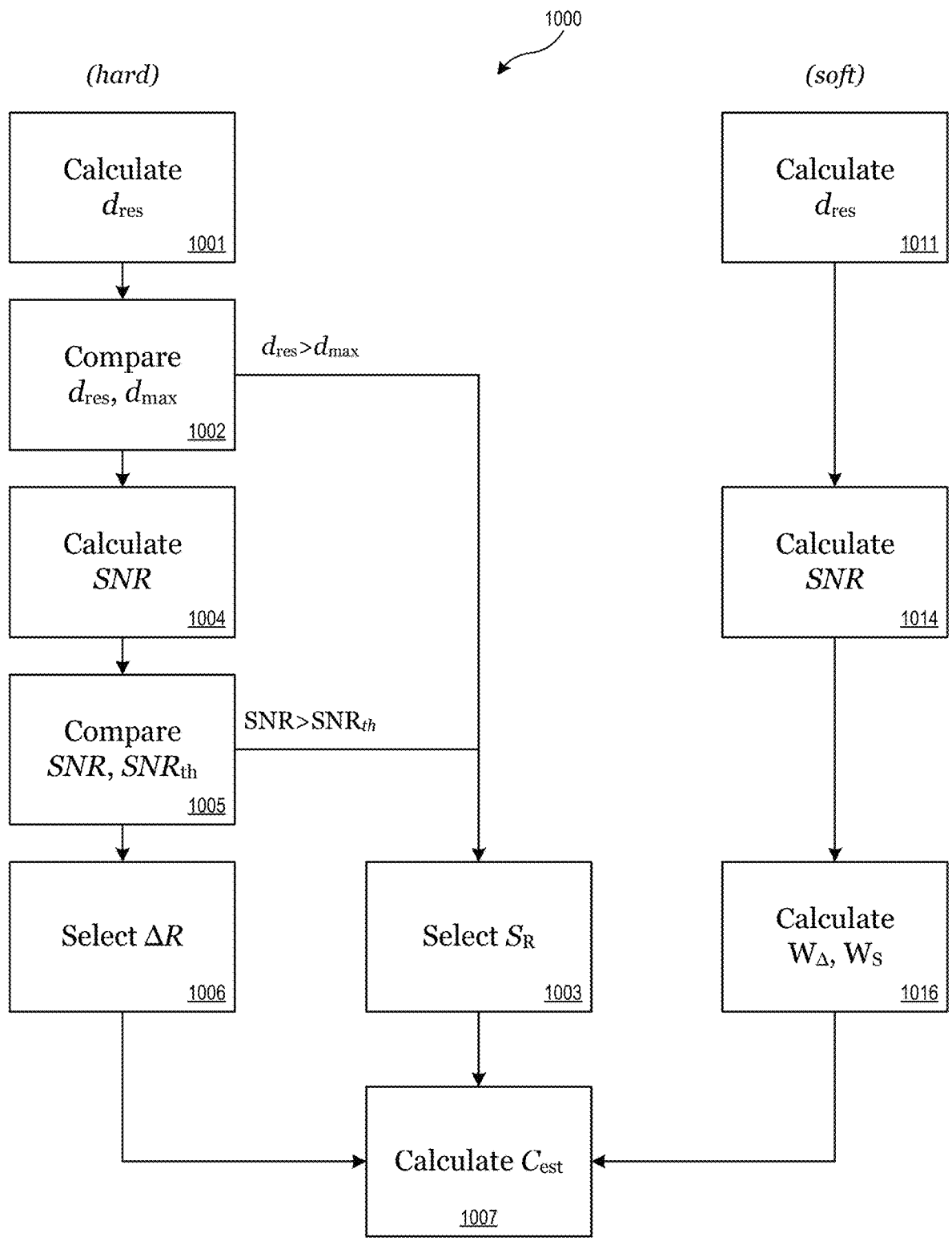
FIG. 10 illustrates an example method of calculating a concentration of a target analyte detected at a sensor by selecting metrics using drift value and a signal-to-noise ratio in accordance with an embodiment of the invention.

FIG. 10 illustrates an example method of calculating a concentration of a target analyte detected at a sensor by selecting metrics using drift value and a signal-to-noise ratio in accordance with an embodiment of the invention. The method of FIG. 10 may be performed by a sensing system as described in other embodiments such as the sensing systems of FIG. 7, 8, or 9, as examples.

Referring to FIG. 10, a method 1000 of calculating a concentration of a target analyte may be performed by a sensing system. The sensing system may be configured to select the metric according to a hard selection paradigm or a soft selection paradigm. In a hard selection paradigm, a single metric may be selected. An example implementation of a hard selection paradigm may be sensing system 800 of FIG. 8. In a soft selection paradigm the sensing system may select a combination of metrics by assigning weights to each metric. An example implementation of a soft selection paradigm may be sensing system 900 of FIG. 9.

The method 1000 includes the following steps. Following the hard selection path, step 1001 includes calculating the residual drift $d_{res}$. After obtaining the residual drift, step 1002 includes comparing dyes to a predetermined maximum residual drift $d_{max}$. If the residual drift is greater than the maximum ($d_{res} > d_{max}$) then the sensing system may select $S_R$ as the metric using a hard selection mechanism in step 1003.

If $d_{res} \leq d_{max}$ in step 1002, the method 1000 continues to step 1004 of calculating a signal-to-noise ratio SNR rather than selecting a metric. For example, SNR may be calculated using the equation $SNR = \Delta R / \sigma_n$. After obtaining an SNR value, the sensing system may compare the signal-to-noise ratio to a signal-to-noise ratio threshold $SNR_{th}$ in step 1005. If the signal-to-noise ratio is greater than the threshold ($SNR > SNR_{th}$) then the sensing system may continue to step 1003 and select $S_R$ as the metric using a hard selection mechanism. After step 1005, if the sensing system determines that the signal-to-noise ratio is not greater than the signal-to-noise ratio threshold ($SNR \leq SNR_{th}$), the sensing system may select the $\Delta R$ metric using a hard selection mechanism in step 1006.

Following the selection of a metric in either step 1003 or step 1006, the sensing system may calculate the concentration of the target analyte in step 1007 using the selected metric. For example, in one embodiment, an estimation of the concentration of a target analyte may be calculated in step 1007 according to equations (1.1) and (1.2) where $K_\Delta$ and $K_S$ are calibration coefficients for the $\Delta R$ and the $S_R$ metric respectively.

$$C_{est} = \frac{\Delta R}{K_\Delta}, \text{ when } \Delta R \text{ is selected} \quad (1.1)$$

$$C_{est} = \frac{S_R}{K_S}, \text{ when } S_R \text{ is selected} \quad (1.2)$$

The calibration coefficients $K_\Delta$ and $K_S$ may be chosen according to specific details of a target analyte and/or the sensing system. In some cases, the calibration coefficients may also be computed or adjusted based on calibration of the sensing system.

Still referring to FIG. 10 and now following the soft selection path of method moo, a sensing system may calculate a residual drift $d_{res}$ in step ion which may be similar to step 1001 of the hard selection path. In contrast to the step 1001, however, there is no comparison step necessary after step 1011. Instead, a signal-to-noise ratio SNR may be calculated in a step 1014 which may be similar to step 1004 of the hard selection path. Since no comparison is needed after step 1014 in the soft selection path, the sensing system may then proceed to calculate weights for each metric in step 1016 according to a soft selection paradigm.

In one possible implementation of a soft selection paradigm, weights may be assigned according to the following equations in which $W_\Delta$ and $W_S$ are weights associated with $\Delta R$ and $S_R$ respectively.

$$W_\Delta = 1 - ceil_1\left(\frac{SNR}{SNR_{th}}\right)^{b_{drift}} = 1 - ceil_1\left(\frac{\Delta R/\sigma_n}{SNR_{th}}\right)^{b_{drift}} \quad (2.1)$$

$$W_S = 1 - W_\Delta \quad (2.2)$$

$$ceil_1(x) = \begin{cases} 1, \text{ for } x \geq 1 \\ x, \text{ otherwise} \end{cases} \quad (2.3)$$

$$b_{drift} = \begin{cases} 0, \text{ if } d_{res} > d_{max} \\ 1, \text{ otherwise} \end{cases} \quad (2.4)$$

In equation (2.1), the weight $W_\Delta$ is calculated by first determining a noise contribution by dividing the signal-to-noise ratio SNR by a signal-to-noise ratio threshold $SNR_{th}$. A ceiling function, shown in equation (2.3), is then applied to the noise contribution to prevent the calculated noise contribution from exceeding a value of one. A drift contribution is then considered by applying a step function, shown in equation (2.4) to the result of the ceiling function. In this case, the drift contribution is a digital function, but other formulations are possible. Equation (2.1) is then evaluated by subtracting the combined noise and drift contributions from one to determine the weight $W_\Delta$. Once $W_\Delta$ is determined, equation (2.2) is evaluated to determine the weight $W_S$.

Continuing the example soft selection mechanism, a concentration $C_{est}$ may then be estimated from the calculated weights in step 1007 using equation (3) where $K_\Delta$ and $K_S$ are calibration coefficients for the $\Delta R$ and the $S_R$ metric respectively.

$$C_{est} = W_\Delta * \left(\frac{\Delta R}{K_\Delta}\right) + W_S * \left(\frac{S_R}{K_S}\right) \quad (3)$$

A sensing system implementing a soft selection mechanism may emulate a hard selection mechanism during steps where the contribution of a single metric is desirable. For example, a residual drift $d_{res}$ greater than $d_{max}$ calculated in step ion will result in $b_{drift}=0$ in equation (2.4) which leads to $W_\Delta=0$ and $W_S=1$ in step 1016 from equations (2.1) and (2.2) respectively. Evaluating equation (3) in step 1007 using $W_\Delta=0$ and $W_S=1$ eliminates the $W_\Delta$ term resulting in concentration equation (3) and reduces it to equation (1.2). Similarly, if the calculated signal-to-noise ratio SNR is greater than $SNR_{th}$ in step 1014, then the ceiling function of equation (2.3) results in $W_\Delta=0$ and $W_S=1$ in step 1016 from equations (2.1) and (2.2). Therefore, in these specific examples, the hard and soft selection mechanisms result in the same concentration estimation equation (1.2) for $d_{res}>d_{max}$ and $SNR>SNR_{th}$. However, in all other scenarios, a combination of the $\Delta R$ metric and the $S_R$ metric are used for the soft selection mechanism while only $\Delta R$ is used according to equation (1.1) for the hard selection mechanism.

In some cases a sensing system may implement a either a hard selection mechanism or a soft selection mechanism. Alternatively, a combination of a hard selection mechanism and a soft selection mechanism may be used. In some cases, the specific implementation of a soft selection mechanism may effectively select a single metric for certain scenarios and may be considered a combination of a hard selection mechanism and a soft selection mechanism. In some cases a soft selection paradigm may refer to any collection of selection implementations in which it is possible for more than one metric to be considered in the concentration estimation equation.

It should be mentioned that the method 1000 described in reference to FIG. 10 is merely an example of a method of calculating a concentration of a target analyte by a sensing system. Various details may be altered based on specific implementation details of a given sensing system performing method 1000. For example, more or fewer parameters may be considered in method 1000. In the case of a hard selection mechanism, additional and/or different comparison steps may be incorporated based on suitable relationships between measured and calculated parameters. In one embodiment, ambient temperature is compared to a threshold value. In one embodiment, humidity is compared to a threshold value. Other suitable parameters for use in comparison steps of method 1000 may be apparent to those of ordinary skill in the art. In the case of a soft selection mechanism, equations (2.1)-(2.4) used to calculate the weights may be altered by adding, removing, and/or changing the parameters. Suitable parameters may be similar to those discussed above with respect to a hard selection paradigm.

In addition to modifying the comparison steps and/or weight equations of method 1000, more than two metrics may be considered by the sensing system for both a hard selection paradigm and a soft selection paradigm. For example, additional comparison and selection steps may be included in method 1000 in a hard selection implementation. For a soft selection implementation using more than two metrics, weights $W_1$ to $W_n$ may calculated and generalized equations (4.1) and (4.2) may be used to calculate a concentration estimation for a target analyte.

$$C_{est} = \sum_{i=1}^{n} W_i \frac{M_i}{K_i} \quad (4.1)$$

$$\sum_{i=1}^{n} W_i = 1 \quad (4.2)$$

In equations, (4.1) and (4.2), a concentration $C_{est}$ is estimated using n metrics $M_i$ and corresponding calibration coefficients $K_i$ weighted using n weights $W_i$. Equation (4.2) may be considered a normalization mechanism and is optional in some cases. The specific number and type of metrics used in method 1000 may be chosen based on specific implementation details of the sensing system and/or the target analyte.

Figure 11:
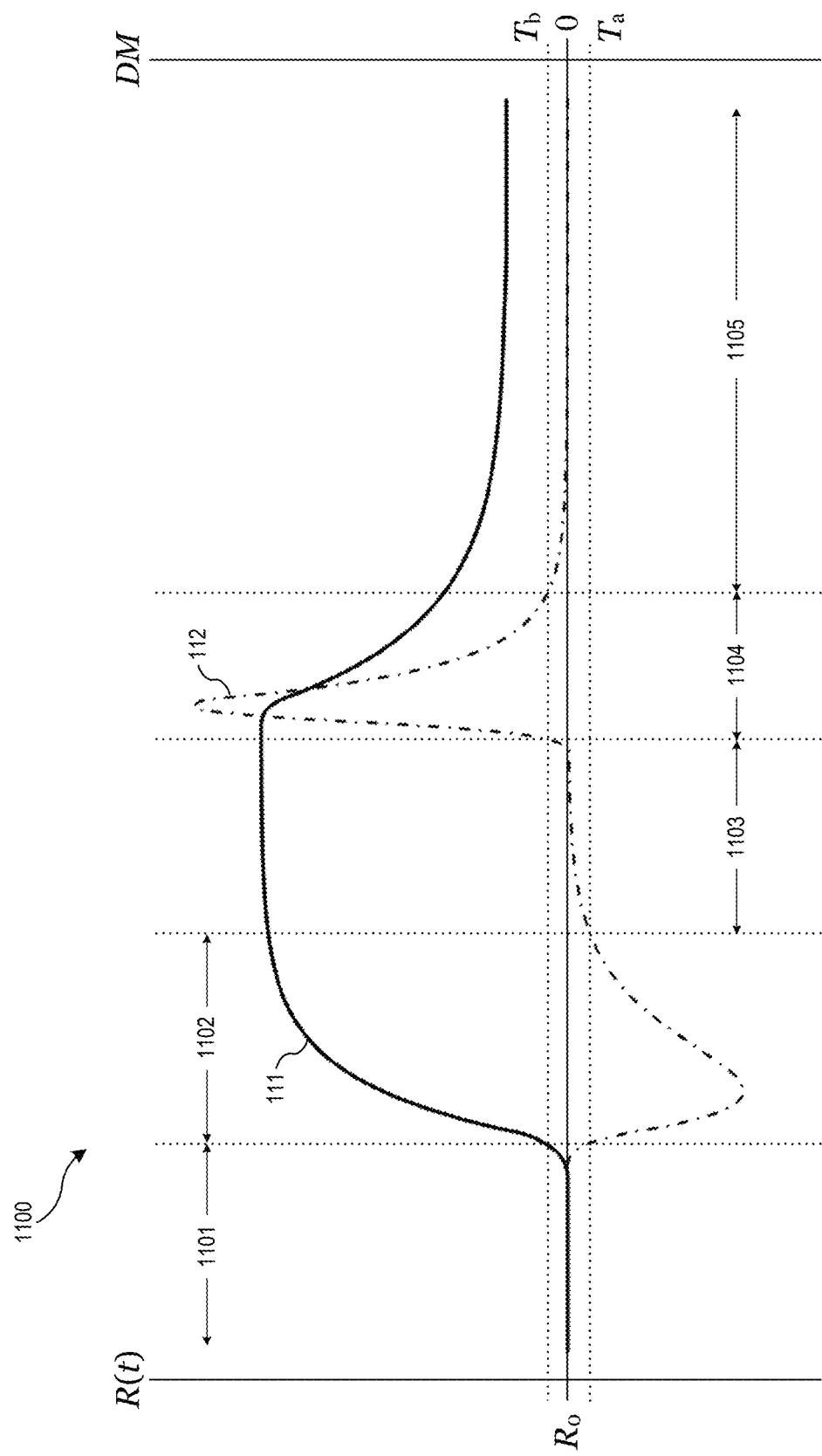
FIG. 11 illustrates a qualitative graph of sensor resistance versus time as detected by a sensing system and a dynamic moment of the sensing system versus time as generated by the sensing system in accordance with an embodiment of the invention.
Figure 12:
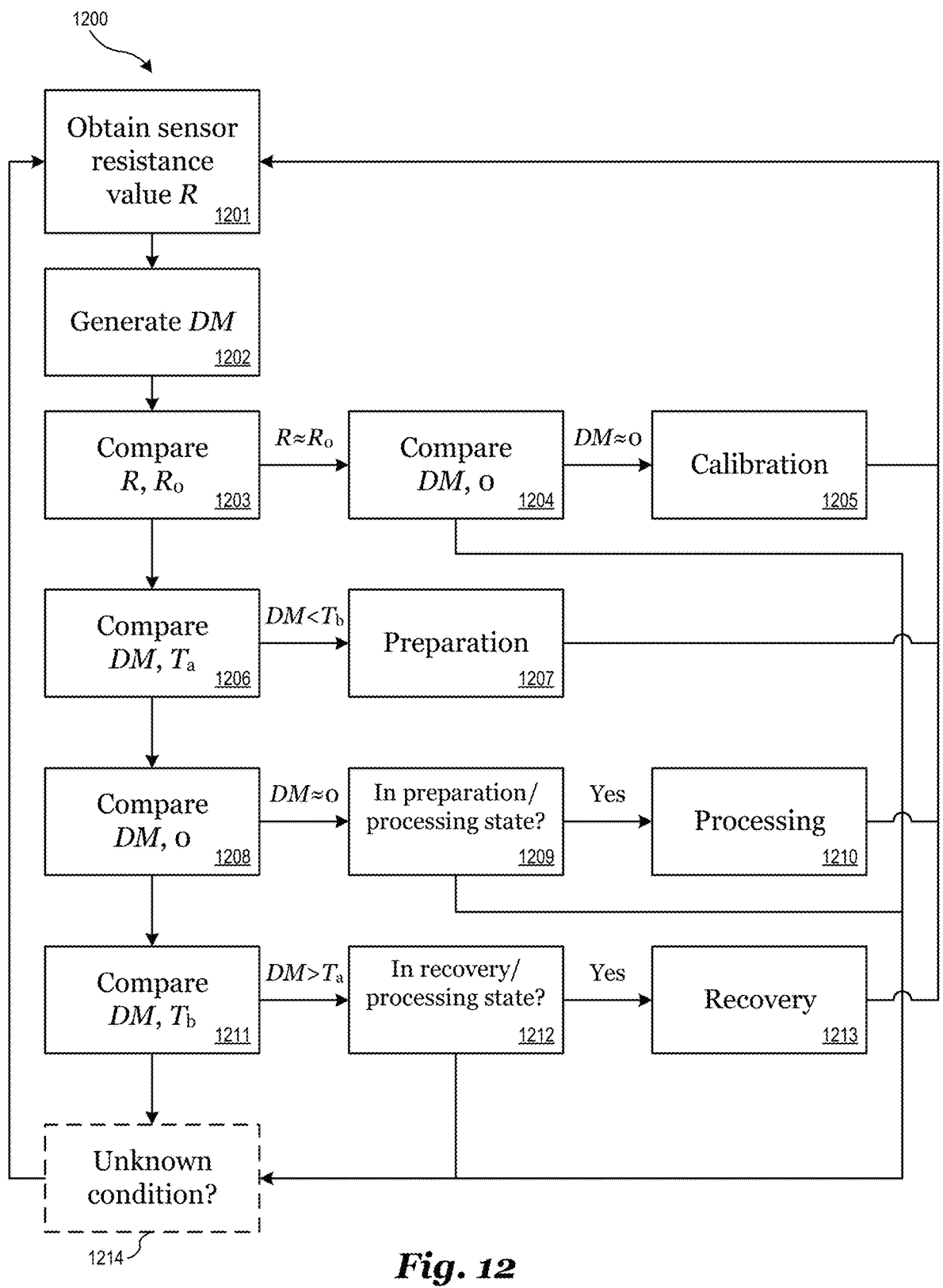
FIG. 12 illustrates an example method of determining the status of a sensing system using sensor resistance and a dynamic moment of the sensing system in accordance with an embodiment of the invention.

Although various sensing systems are described herein for the specific case of using a derivative of a resistance value as a second metric for the calculating an estimated concentration, other metrics are possible. For example, a dynamic moment of the sensing system may be used. As previously described in reference to FIG. 4, $Sig_2$ 42 of sensing system 400 may be a dynamic moment of the system. FIGS. 11 and 12 illustrate a graph and a method corresponding to an example sensing system that uses a dynamic moment as a second metric.

FIG. 11 illustrates a qualitative graph of sensor resistance versus time as detected by a sensing system and a dynamic moment of the sensing system versus time as generated by the sensing system in accordance with an embodiment of the invention. The graph of FIG. 11 may be a representative response of a sensing system as described in other embodiments such as sensing system 400 of FIG. 4, for example.

Referring to FIG. 11, the sensor resistance R(t) curve 111 and the dynamic moment DM curve 112 are plotted as a function of time t in graph 1100. Various dynamic moments may be calculated. The specific dynamic moment used may depend on specific implementation details of the sensing system. For example, in graph 1100, DM is calculated using equation (5), but other dynamic moments are possible.

$$DM = \frac{\sqrt{2}}{2n} \sum_{i=0}^{n} (x_i^2 y_i - x_i y_i^2) \quad (5)$$

In equation (5), n=1, $x_0(t)=R(t)$, $x_1(t)=R'(t)$, and $y_i(t)=x_i(t+\tau)$ where $\tau$ is a constant time added to the variable time t More or fewer phase space variables $x_i(t)$ may be used in other implementations. Although the derivative of the resistance is used for $x_1$ in this specific example, other metrics may be used in other embodiments.

Similar to graph 600 of FIG. 6, graph 1100 has five intervals defined by the relationship between the dynamic moment DM and threshold values $T_a$ and $T_b$. In contrast to graph 600, $T_a$ is negative and $T_b$ is positive. Interval 1101 may be interpreted as a calibration interval by the sensing system. As the dynamic moment curve 112 decreases below $T_a$, the sensing system may determine that the system is in a new interval 1102 which may be interpreted as a preparation interval. Once the dynamic moment curve 112 returns to a value above $T_a$, the sensing system may determine that the system is in interval 1103 which may be interpreted as a processing internal by the sensing system. Similarly, $T_b$ is used by the sensing system as a comparison value to determine that the sensing system is in an interval 1104 when DM is greater than $T_b$. Interval 1104 may be interpreted as a recovery interval by the sensing system. Once the value of DM returns to below $T_b$ the sensing system may determine that the system is in a new interval 1105. Interval 1105 may be interpreted as a calibration interval or a processing interval depending on specific parameters and implementation details.

FIG. 12 illustrates an example method of determining the status of a sensing system using sensor resistance and a dynamic moment of the sensing system in accordance with an embodiment of the invention. The method of FIG. 12 may be performed by a sensing system as described in other embodiments such as the sensing system 400 of FIG. 4, for example.

Referring to FIG. 12, the method 1200 of determining the status of a sensing system is similar to method 500 of FIG. 5 except that a dynamic moment DM is used for the series of comparisons instead of a derivative of the resistance R'. The resistance R and the dynamic moment DM are generated in steps 1201 and 1202 respectively. After generation of R and DM, several comparisons between R, DM, $R_0$, $T_a$, $T_b$, and zero may be made by the sensing system in steps 1203, 1204, 1206, 1208, and 1211. The sensing system may also check the current state of the sensing system in steps 1209 and 1212. As previously described in reference to FIG. 11, the sensing system may then determine that the system is in a calibration interval, preparation interval, processing interval, or a recovery interval according to the results of the series of comparisons in steps 1205, 1207, 1210, and 1213 respectively.

After the determination of an interval, the sensing system may return to step 1201 and repeat the method. As in method 500, various comparison steps may lead to an optional unknown condition step 1214 which may be handled on a case by case basis by the sensing system. After the unknown condition is handled, the sensing system may return to step 1201.

Figure 13:
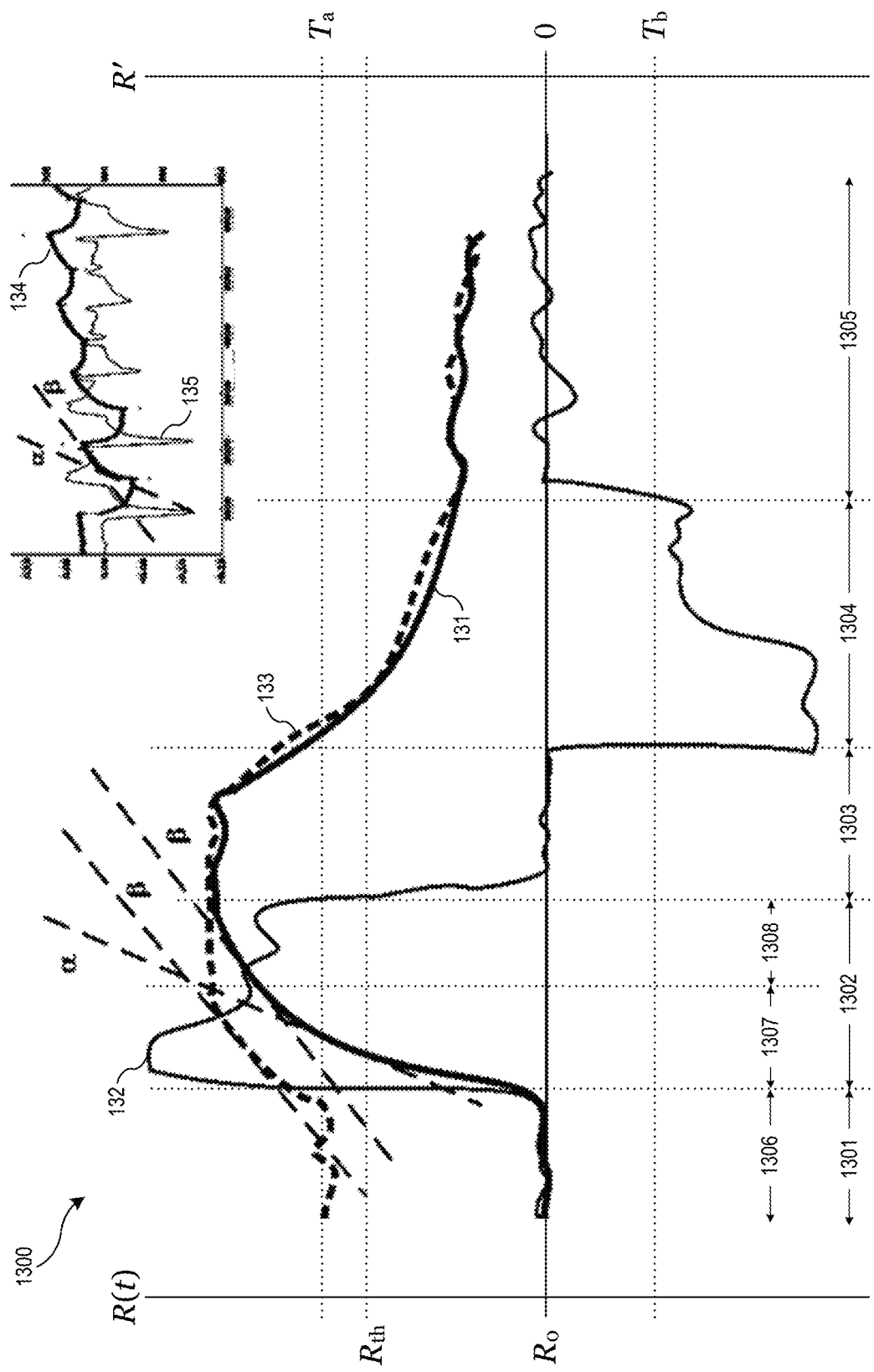
FIG. 13 illustrates a graph of sensor resistance versus time as detected by a sensor beginning in an environment with no target analyte and also as detected by a sensor beginning in an environment with a non-zero concentration of the target analyte in accordance with an embodiment of the invention.

FIG. 13 illustrates a graph of sensor resistance versus time as detected by a sensor beginning in an environment with no target analyte and also as detected by a sensor beginning in an environment with a non-zero concentration of the target analyte in accordance with an embodiment of the invention. The graph of FIG. 13 may be a representative response of a sensing system as described in other embodiments such as sensing system 400 of FIG. 4, for example.

Referring to FIG. 13, the sensor resistance R(t) curve 131 and the slope of the resistance R'(t) curve 132 are plotted as a function of time t in graph 1300. A smaller inset graph including an additional sensor resistance R(t) curve 134 and corresponding slope of the resistance R'(t) curve 135 are also illustrated for example purposes. The graph 1300 includes five intervals 1301, 1302, 1303, 1304, and 1305 analogous to intervals 601, 602, 603, 604, and 605 of graph 600.

In addition to these intervals, however, graph 1300 also includes an interval 1307 associated with a linear approximation of the resistance slope α and an interval 1308 associated with a linear approximation of the resistance slope β. The approximately linear slopes α and β may represent different regimes of the sensing system. For example, interval 1307 may be defined by the approximately linear slope α which may occur as a result of the sensor adsorbing a variety of species in the ambient environment which may or may not include a target analyte. The baseline resistance $R_0$ may be determined when the sensing system is in an inert environment. However, in practice, the sensing system may be located in an environment where are variety of species may interact with the sensing system. The linear slope α may represent the system approaching equilibrium with the ambient environment. At equilibrium, the resistance response of the system may be approximately constant. This constant resistance may represent a constant concentration of a target analyte or a constant background caused by other species in the ambient environment of the sensing system.

Interval 1308 may be defined by the approximately linear slope β which may occur as a result of the sensor adsorbing a target analyte that is present at a measureable concentration in the environment. For example, after a certain threshold resistance $R_{th}$ a sensing system may have a specific response to a target analyte that is approximately linear with a slope of β. After the sensing system has reached an approximate equilibrium with the environment in interval 1307, the interval 1308 may be dominated by specific adsorption of the target species.

A second resistance R(t) curve 133 is also plotted as an example of the resistance response of a sensing system in an ambient environment that includes one or more species that interact with the sensing system. The second resistance R(t) curve 133 has an interval 1306 that corresponds with interval 1301 of resistance R(t) curve 1301. However, during interval 1306, the resistance is above a threshold value of $R_{th}$. The sensing system may be configured to determine this and interpret the appropriate interval 1307 or 1308 when the slope of the resistance R'(t) increases.

Figure 14:
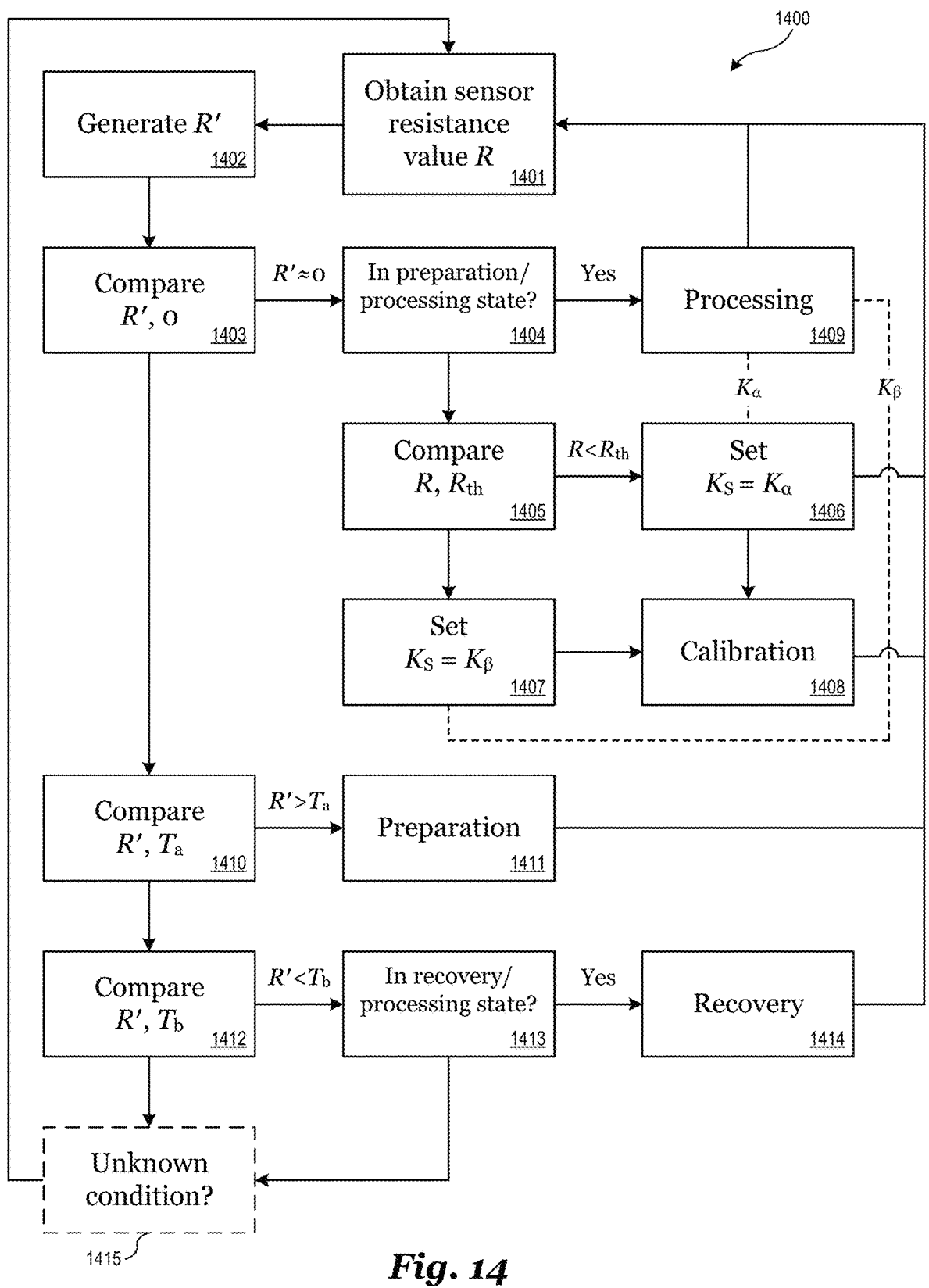
FIG. 14 illustrates an example method of determining the status of a sensing system using sensor resistance, the derivative of the sensor resistance, and a resistance threshold in accordance with an embodiment of the invention.

FIG. 14 illustrates an example method of determining the status of a sensing system using sensor resistance, the derivative of the sensor resistance, and a resistance threshold in accordance with an embodiment of the invention. The method of FIG. 14 may be performed by a sensing system as described in other embodiments such as the sensing system 400 of FIG. 4, for example. The method of FIG. 14 may be similar to method 500 of FIG. 5 except that the preparation interval may be split into one or more regimes corresponding to one or more approximately linear slopes α, β, etc.

Referring to FIG. 14, a method 1400 of determining the status of a sensing system includes the following steps. Step 1401 includes obtaining a sensor resistance value R. After obtaining R, the sensing system may use R to generate the derivative of the resistance R' in step 1402. The sensing system may then compare R' to zero in step 1403. If the sensing system determines that the slope of the resistance R' is approximately zero (R'≈0) then the sensing system is currently measuring a substantially constant resistance. However, as previously described, a substantially constant resistance may indicate either a calibration interval or a processing interval. Therefore, after determining that R'≈0 the sensing system may further check if the sensing system is currently in a preparation or processing state in step 1404.

If the sensing system is not in a preparation state or a processing state then the sensing system can determine that the slope of the resistance R' was not greater than $T_a$ in the interval immediately preceding this interval. This may indicate to the sensing system that the system is in a calibration interval. However, as discussed above in reference to graph 1300 of FIG. 13, the calibration interval may include multiple regimes defined by approximately linear slopes. For example, there may be two regimes in the calibration interval defined by linear slope α and linear slope β.

The sensing system may compare the resistance value R to a predetermined threshold value $R_{th}$ in step 1405 in order to determine which linear slope regime currently applies to the sensing system. If $R<R_{th}$ then the calibration coefficient for the slope $K_S$ is set to a calibration coefficient associated with α ($K_S=K_\alpha$) in step 1406. If $R \leq R_{th}$ then $K_S$ is set to a calibration coefficient associated with β ($K_S=K_\beta$) in step 1407. After either step 1406 or 1407, the sensing system determines that the status of the sensing system is a calibration interval in step 1408.

If, during step 1404, the sensing system confirms that the sensing system is in the preparation state or the processing state, the sensing system determines that the current status of the sensing system is the processing interval in step 1409. While processing, the sensing system may use the current stored value of $K_S$. For example, the dashed lines drawn from each of step 1406 and step 1407 indicate that the sensing system will use $K_\alpha$ if previously set in step 1406 or $K_\beta$ if previously set in step 1407.

If the sensing system determines that R'≠0 in step 1403, the sensing system may compare R' and $T_a$ in step 1410. The sensing system may then determine that the current status of the sensing system is a preparation interval in step 1411 when $R'>T_a$. If a preparation interval is not identified by the sensing system, then R' may be compared to $T_b$ in step 1412. If the sensing system determines that $R'<T_b$ in step 1412, then the sensing system may check if the current state is either the recovery state or the processing state. If the sensing system is in one of the recovery state or the processing state, the sensing system may determine that the current status of the system is the recovery interval in step 1414. As previously described, unknown conditions may optionally be handled in a step 1415 before returning to step 1401. Additionally, after a positive determination of the current status of the sensing system, the sensing system may return to step 1401 in order to continually monitor the status of the sensing system.

Figure 15:
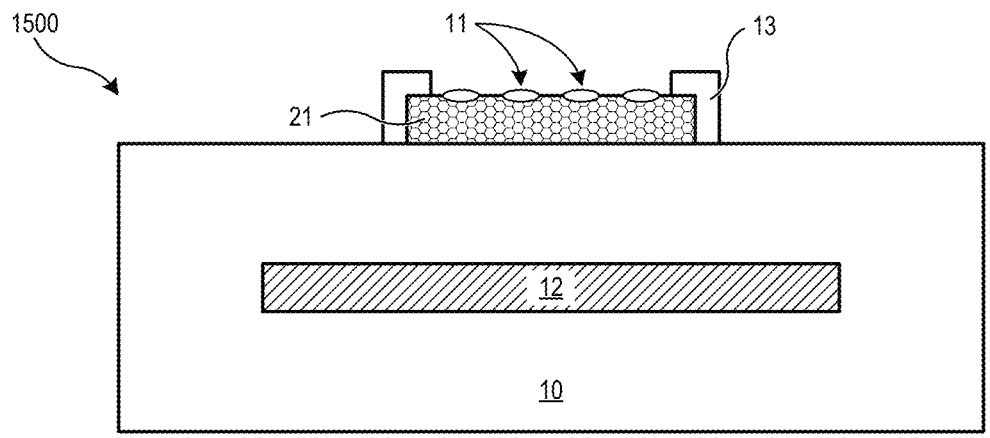
FIG. 15 illustrates an example sensing array including a substrate, a heating element, and one or more sensors in accordance with an embodiment of the invention.

FIG. 15 illustrates an example sensing array including a substrate, a heating element, and one or more sensors in accordance with an embodiment of the invention. The sensing array of FIG. 15 may be included in sensing systems as described in other embodiments such as sensing system 200 of FIG. 2, for example.

Referring to FIG. 15, a sensing array 1500 includes one or more sensors 21 disposed on a substrate 10. The sensor 21 may be any suitable type of sensor such as a chemical sensor configured to detect a target analyte or group of target analytes. In various embodiments, the sensor 21 is a gas sensor. In some embodiments, the gas sensor is a resistive gas sensor, and in one embodiment, sensor 21 is a reduced graphene oxide gas sensor. The reduced graphene oxide gas sensor may generate sensing events by monitoring the change in resistance of one or more sheets of graphene, which is modulated by gas molecules being adsorbed and desorbed from the surface of the graphene. The sensor resistance may decrease when adsorbed gas species provide donor electrons to the graphene surface. Alternatively, the resistance may decrease when adsorbed gas species draw electrons away from the path of conduction.

The transduction method for the reduced graphene oxide gas sensor may also be different in various embodiments. For example, rather than a resistive gas sensor, sensor 21 may be a capacitive gas sensor and is a graphene-based capacitive gas sensor in one embodiment. Other possible transduction methods may be apparent to those of ordinary skill in the art and include work function monitoring, inversion n-type to p-type, and others.

Sensor 21 may be configured to have selectivity towards a target analyte. For example, sensor 21 may selectively sense concentrations of volatile organic compounds (VOCs) in the ambient atmosphere. In various embodiments, sensor 21 may be configured to sense volatile gases such as hydrocarbons, methylene chloride, formaldehyde, and the like.

The sensor 21 may be suspended between two or more electrodes 13. The electrodes 13 may include a conductive material and may be a patterned metal in various embodiments. For example, the electrodes 13 may include copper (Cu), silver (Ag), gold (Au), aluminum (Al), tungsten (W), and the like.

In some embodiments, the sensor 21 may also include surface modifications 11. The surface modifications 11 may be chemical groups attached to the surface of sensor 21 to increase the sensitivity of sensor 21 to target analytes and/or reduce the sensitivity of sensor 21 to environmental factors or species other than target analytes. In other embodiments, the surface modifications 11 may be a protective coating and may cover all or most of the sensor 21.

The substrate 10 may be any suitable substrate. In various embodiments, substrate 10 is a laminate substrate and is a printed circuit board in one embodiment. In other embodiments, substrate 10 is a semiconductor substrate and is part of a monolithic integrated circuit chip including sensor 21. In one embodiment, substrate 10 is a silicon substrate and sensor 21 is included in an integrated circuit. In another embodiment, substrate 10 is a ceramic substrate. Substrate 10 may also be a metallic substrate or include a metallic substrate. In some embodiments, substrate 10 may be packaged to form a sensor package including sensor 21.

A heating element 12 may be included on or within substrate 10. The heating element 12 may heat the sensor 21 and sensing array 1500 in order to maintain an optimal operating temperature or range of operating temperatures. For example, the heating element 12 may heat the sensor 21 to 200° C. in one embodiment. In another embodiment, the heating element 12 may heat the sensor 21 to 400° C. In the specific case of a resistive gas sensor, the temperature may need to be elevated to facilitate desorption of gas molecules for continued sensing. In some cases, refresh cycles may be used to heat the sensor 21 to a temperature well above the normal operating temperature in order to remove all species from the surface of sensor 21 before beginning a new data acquisition period.

The heating element 12 may also be used as a reference for baseline variation of sensor 21. For example, the resistance of heating element 12 may be recorded periodically during data acquisition periods and used as reference data points when determining baseline drift of sensor 21.

The heating element 12 may be a metal conductor in one embodiment. In other embodiments, the heating element 12 may be a microelectromechanical systems (MEMS) heater integrated into a semiconductor substrate. The heating element 12 and/or sensor 21 may also be suspended over an opening in substrate 10. This may facilitate increased interaction with the ambient atmosphere as well as reduce heat loss in the heating element 12.

Figure 16:
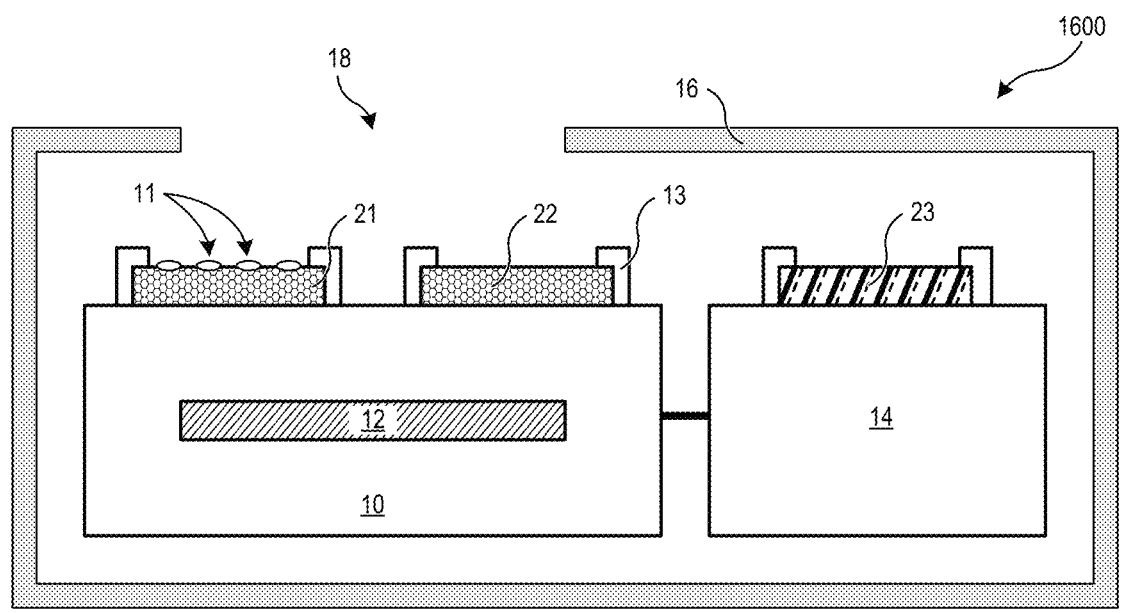
FIG. 16 illustrates another example sensing array including a substrate, a heating element, a sensor, an environmental sensor, and a reference sensor where the environmental sensor is located on a second substrate in accordance with an embodiment of the invention.

FIG. 16 illustrates another example sensing array including a substrate, a heating element, a sensor, an environmental sensor, and a reference sensor where the environmental sensor is located on a second substrate in accordance with an embodiment of the invention. The sensing array of FIG. 16 may be included in sensing systems as described in other embodiments such as sensing system 200 of FIG. 2, for example.

Referring to FIG. 16, a sensor device 1600 includes a sensor 21 and a heating element 12 attached to a substrate 10 as previously described. However sensing array 1600 differs from sensing array 1600 in that a reference sensor 22 is attached to substrate 10 and an environmental sensor 23 is attached to a second substrate 14. The substrate 10 is operatively coupled to the second substrate 14 and both are contained in a package 16.

The environmental sensor 23 may be a temperature sensor, humidity sensor, pressure sensor, and the like. The environmental sensor 23 may be configured to measure reference data points to for use in correcting baseline drift of sensor 21. The reference sensor 22 may be sufficiently similar in structure or function to sensor 21 so as to provide reference data points for use in correcting baseline drift of sensor 21.

For example, sensor 21 and reference sensor 22 may both be gas sensors, but reference sensor 22 may not include surface modifications 11. Alternatively, the surface of sensor 21 may be bare while the surface of reference sensor 22 is coated or otherwise modified to be unresponsive to the target analyte of sensor 21. In this way, the contribution of the sensing target may be removed from the signal of the reference sensor 22 and only the effects of environmental factors remain. Significant correlation between the sensor 21 and the reference sensor 22 may then be primarily caused by environmental factors and reflect baseline drift in both sensors.

The second substrate 14 may include a processor such as an ASIC or an FPGA. The processor may be configured to perform any of the method steps as described in previous embodiments. The substrate 10 and the second substrate 14 may be rigidly attached to the package 60. However, in some embodiments, the substrate 10 and the second substrate 14 may be elastically attached to the package 60.

The package 16 includes an opening 18 which facilitates interactions of sensor 21, reference sensor 22, and environmental sensor 23 with the ambient environment. It should be noted that although package 16 and opening 18 are only illustrated in FIG. 16, package 16 and opening 18 may be included in all embodiment sensing systems described herein and also other sensing systems as apparent to those of ordinary skill in the art.

Example embodiments of the present invention are summarized here. Other embodiments can also be understood from the entirety of the specification as well as the claims filed herein.

Example 1. A method of gas sensing, the method including: obtaining, by a gas sensor, a first signal indicating a response of the gas sensor to a concentration of a target gas at the gas sensor; generating one or more second signals according to the first signal; calculating a first weight value corresponding to the first signal; calculating one or more second weight values corresponding to each of the one or more second signals; and calculating an estimated concentration of the target gas at the gas sensor according to the first weight value and the one or more second weight values.

Example 2. The method of example 1, where the gas sensor is a resistive gas sensor.

Example 3. The method of one of examples 1 and 2, where the gas sensor includes graphene.

Example 4. The method of one of examples 1 to 3, where the first signal includes a resistance of the gas sensor.

Example 5. The method of one of examples 1 to 4, where the one or more second signals include a derivative of the first signal.

Example 6. The method of one of examples 1 to 5, where the one or more second signals include an integral of the first signal.

Example 7. The method of one of examples 1 to 6, further including: calculating a signal-to-noise ratio (SNR) of the first signal by dividing the first signal by a standard deviation of the first signal calculated over a period of time; determining a ratio between the SNR and a predetermined SNR threshold; and where the first weight value and the one or more second weight values are calculated according to the ratio.

Example 8. The method of one of examples 1 to 7, further including: calculating a drift value of the first signal; comparing the drift value to a predetermined drift maximum; and where the first weight value and the one or more second weight values are calculated according to the comparison.

Example 9. A method of gas sensing, the method including: obtaining, by a gas sensor, a first signal indicating a response of the gas sensor to a concentration of a target gas at the gas sensor; generating one or more second signals according to the first signal; determining a first condition in which a concentration of the target gas is increasing at the gas sensor using the first signal and the one or more second signals; determining a second condition in which the concentration at the gas sensor is substantially constant using the first signal and the one or more second signals, the second condition occurring after the first condition; and calculating a concentration value of the target gas according to the first signal and the one or more second signals, the calculating performed while the concentration is substantially constant.

Example 10. The method of example 9, where the first signal includes a resistance of the gas sensor.

Example 11. The method of one of examples 9 and 10, where the one or more second signals include a derivative of the first signal.

Example 12. The method of one of examples 9 to 11, where the one or more second signals include an integral of the first signal.

Example 13. The method of one of examples 9 to 12, further including: determining a third condition in which the concentration at the gas sensor is substantially constant and approximately zero using the first signal and the one or more second signals; and calibrating the gas sensor while the concentration is substantially constant and approximately zero.

Example 14. The method of one of examples 9 to 13, further including: determining a third condition in which the concentration at the gas sensor is decreasing using the first signal and the one or more second signals, the third condition occurring after the second condition.

Example 15. A gas sensing system including: a gas sensor disposed on a first substrate, the gas sensor being configured to detect a target gas and generate a first signal indicating a response of the gas sensor to a concentration of a target gas at the gas sensor; a processor operatively coupled to the gas sensor; and a memory storing a program to be executed by the processor, the program including instructions for generating one or more second signals according to the first signal, calculating a first weight value corresponding to the first signal, calculating one or more second weight values corresponding to each of the one or more second signals, and calculating a concentration of the target gas at the gas sensor according to the first weight value and the one or more second weight values.

Example 16. The gas sensing system of example 15, where the gas sensor is a resistive gas sensor.

Example 17. The gas sensing system of one of examples 15 and 16, where the gas sensor includes graphene.

Example 18. The gas sensing system of one of examples 15 to 17, where the first signal includes a resistance of the gas sensor.

Example 19. The gas sensing system of one of examples 15 to 18, where the one or more second signals include a derivative of the first signal.

Example 20. The gas sensing system of one of examples 15 to 19, where the one or more second signals include an integral of the first signal.

Example 21. The gas sensing system of one of examples 15 to 20, where the program includes further instructions for calculating a signal-to-noise ratio (SNR) of the first signal by dividing the first signal by a standard deviation of the first signal calculated over a period of time, and determining a ratio between the SNR and a predetermined SNR threshold, where the first weight value and the one or more second weight values are calculated according to the ratio.

Example 22. The gas sensing system of one of examples 15 to 21, where the program includes further instructions for calculating a drift value of the first signal, and comparing the drift value to a predetermined drift maximum, where the first weight value and the one or more second weight values are calculated according to the comparison.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method of gas sensing performed by a processor electrically coupled to a gas sensor, the method comprising:
    receiving a first electrical signal obtained by the gas sensor and indicating a response of the gas sensor to a concentration of a target gas at the gas sensor;
    generating one or more second electrical signals using the first electrical signal;
    determining a signal-to-noise ratio (SNR) of the first electrical signal by dividing the first electrical signal by a standard deviation of the first electrical signal calculated over a period of time;
    comparing the SNR to a predetermined SNR threshold;
    in response to determining that the SNR is greater than the predetermined SNR threshold, selecting a single electrical signal of the one or more second electrical signals as a metric for calculating an estimated value of the concentration according to a hard selection paradigm comprising
        setting a first weight value corresponding to the first electrical signal to zero,
        setting a second weight value corresponding to the single electrical signal to one, and
        setting remaining weight values corresponding to each of the remaining one or more electrical signals to zero;
    in response to determining that the SNR is not greater than the predetermined SNR threshold, selecting the first electrical signal and the one or more second electrical signals as metrics for calculating the estimated value of the concentration according to a soft selection paradigm comprising
        determining the first weight value according to the SNR, and
        determining the second weight value and any remaining weight values according to the one or more second electrical signals;
    calculating the estimated value of the concentration of the target gas at the gas sensor using the first weight value, the second weight value, and any remaining weight values; and
    outputting a third electrical signal indicating the estimated value of the concentration of the target gas.

2. The method of claim 1, wherein the gas sensor is a resistive gas sensor.

3. The method of claim 1, wherein the first electrical signal comprises a resistance of the gas sensor.

4. The method of claim 1, wherein the one or more second electrical signals comprise a derivative of the first electrical signal.

5. The method of claim 1, wherein the one or more second electrical signals comprise an integral of the first electrical signal.

6. The method of claim 1, further comprising:
    determining a first condition in which the concentration of the target gas is increasing at the gas sensor using the first electrical signal and the one or more second electrical signals;
    determining a second condition in which the concentration at the gas sensor is substantially constant using the first electrical signal and the one or more second electrical signals, the second condition occurring after the first condition; and
    wherein calculating the estimated value of the concentration of the target gas at the gas sensor is performed while the concentration is substantially constant.

7. The method of claim 6, further comprising:
    determining a third condition in which the concentration at the gas sensor is substantially constant and approximately zero using the first electrical signal and the one or more second electrical signals; and
    calibrating the gas sensor while the concentration is substantially constant and approximately zero.

8. The method of claim 6, further comprising:
    determining a third condition in which the concentration at the gas sensor is decreasing using the first electrical signal and the one or more second electrical signals, the third condition occurring after the second condition.

9. The method of claim 1, wherein:
    calculating the estimated value of the concentration comprises multiplying the first electrical signal by the first weight value and multiplying the one or more second electrical signals by the corresponding second weight value and any remaining weight values.

10. The method of claim 1, wherein the one or more second electrical signals comprise a dynamic moment calculated using the first electrical signal.

11. The method of claim 1, wherein the one or more second electrical signals comprise an energy vector calculated using multiple electrical signals obtained by a sensing array of the gas sensor.

12. The method of claim 1, wherein calculating the estimated value comprises directly calculating the estimated value of the target gas at the gas sensor from an equation including the first electrical signal, the one or more second electrical signals, the first weight value, and the second weight value and any remaining weight values.

13. The method of claim 12, wherein the equation is $$C_{est} = \sum_{i=1}^{n} W_i \frac{M_i}{K_i},$$

and wherein $W_i$ are weight values, $M_i$ are metrics, $K_i$ are calibration coefficients, and i is an index corresponding to the first electrical signal and each of the one or more second electrical signals.

14. The method of claim 1, further comprising:
determining a drift value of the first electrical signal;
before comparing the SNR to the predetermined SNR threshold, comparing the drift value to a predetermined drift maximum;
in response to determining that the drift value is greater than the predetermined drift maximum and before comparing the SNR to the predetermined SNR threshold, selecting the single electrical signal as the metric for calculating the estimated value of the concentration according to the hard selection paradigm; and
in response to determining that the drift value is not greater than the predetermined drift maximum, proceeding to the step of comparing the SNR to the predetermined SNR threshold.

15. A gas sensing system comprising:
a gas sensor disposed on a first substrate, the gas sensor being configured to detect a target gas and generate a first electrical signal indicating a response of the gas sensor to a concentration of the target gas at the gas sensor;
a processor operatively coupled to the gas sensor; and
a memory storing a program to be executed by the processor, the program comprising instructions for
generating one or more second electrical signals using the first electrical signal,
determining a signal-to-noise ratio (SNR) of the first electrical signal by dividing the first electrical signal by a standard deviation of the first electrical signal calculated over a period of time,
comparing the SNR to a predetermined SNR threshold,
in response to determining that the SNR is greater than the predetermined SNR threshold, selecting the first electrical signal as a metric for calculating an estimated value of the concentration according to a hard selection paradigm comprising
setting a first weight value corresponding to the first electrical signal to zero,
setting a second weight value corresponding to a single electrical signal of the one or more second electrical signals to one, and
setting remaining weight values corresponding to each of the remaining one or more electrical signals to zero,
in response to determining that the SNR is not greater than the predetermined SNR threshold, selecting the first electrical signal and the one or more second electrical signals as metrics for calculating the estimated value of the concentration according to a soft selection Paradigm comprising
determining the first weight value according to the SNR, and
determining the second weight value and any remaining weight values according to the one or more second electrical signals,
calculating the estimated value of the concentration of the target gas at the gas sensor using the first weight value, the second weight value, and any remaining weight values, and
outputting a third electrical signal indicating the estimated value of the concentration of the target gas.

16. The gas sensing system of claim 15, wherein the gas sensor is a resistive gas sensor.

17. The gas sensing system of claim 15, wherein the gas sensor comprises graphene.

18. The gas sensing system of claim 15, wherein the first electrical signal comprises a resistance of the gas sensor.

19. The gas sensing system of claim 15, wherein the one or more second electrical signals comprise a derivative of the first electrical signal.

20. The gas sensing system of claim 15, wherein the one or more second electrical signals comprise an integral of the first electrical signal.

21. A method of gas sensing performed by a processor electrically coupled to a gas sensor, the method comprising:
receiving a first electrical signal obtained by the gas sensor and indicating a response of the gas sensor to a concentration of a target gas at the gas sensor;
generating one or more second electrical signals using the first electrical signal;
determining a drift value of the first electrical signal;
comparing the drift value to a predetermined drift maximum;
in response to determining that the drift value is greater than the predetermined drift maximum, selecting a single electrical signal of the one or more second electrical signals as a metric for calculating an estimated value of the concentration according to a hard selection paradigm comprising
setting a first weight value corresponding to the first electrical signal to zero,
setting a second weight value corresponding to the single electrical signal to one, and
setting remaining weight values corresponding to each of the remaining one or more electrical signals to zero;
in response to determining that the drift value is not greater than the predetermined drift maximum, selecting the first electrical signal and the one or more second electrical signals as metrics for calculating the estimated value of the concentration according to a soft selection paradigm comprising
determining the first weight value according to the drift value, and
determining the second weight value and any remaining weight values according to the one or more second electrical signals;
calculating the estimated value of the concentration of the target gas at the gas sensor using the first weight value, the second weight value, and any remaining weight values; and
outputting a third electrical signal indicating the estimated value of the concentration of the target gas.

22. A gas sensing system comprising:
a gas sensor disposed on a first substrate, the gas sensor being configured to detect a target gas and generate a first electrical signal indicating a response of the gas sensor to a concentration of the target gas at the gas sensor;

a processor operatively coupled to the gas sensor; and
a memory storing a program to be executed by the processor, the program comprising instructions for
generating one or more second electrical signals using the first electrical signal,
determining a drift value of the first electrical signal,
comparing the drift value to a predetermined drift maximum,
in response to determining that the drift value is greater than the predetermined drift maximum, selecting a single electrical signal of the one or more second electrical signals as a metric for calculating an estimated value of the concentration according to a hard selection paradigm comprising
setting a first weight value corresponding to the first electrical signal to zero,
setting a second-weight value corresponding to the single electrical signal to one, and
setting remaining weight values corresponding to each of the remaining one or more electrical signals to zero,
in response to determining that the drift value is not greater than the predetermined drift maximum, selecting the first electrical signal and the one or more second electrical signals as metrics for calculating the estimated value of the concentration according to a soft selection paradigm comprising
determining the first weight value according to the drift value, and
determining the second weight value and any remaining weight values according to the one or more second electrical signals,
calculating the estimated value of the concentration of the target gas at the gas sensor using the first weight value, the second weight value, and any remaining weight values, and
outputting a third electrical signal indicating the estimated value of the concentration of the target gas.

* * * * *